(12) United States Patent
Gerhard et al.

(10) Patent No.: US 9,090,676 B2
(45) Date of Patent: Jul. 28, 2015

(54) METHOD FOR TREATING HELICOBACTER PYLORI INFECTIONS

(75) Inventors: Markus Gerhard, München (DE); Christian Schmees, Rottweil (DE); Christian Prinz, Wuppertal (DE)

(73) Assignee: IMEVAX GMBH (DE)

( * ) Notice: Subject to any disclaimer, the term of this patent is extended or adjusted under 35 U.S.C. 154(b) by 0 days.

(21) Appl. No.: 12/446,226

(22) PCT Filed: Oct. 19, 2007

(86) PCT No.: PCT/EP2007/009106
§ 371 (c)(1), (2), (4) Date: Apr. 17, 2009

(87) PCT Pub. No.: WO2008/046650
PCT Pub. Date: Apr. 24, 2008

(65) Prior Publication Data
US 2010/0034846 A1 Feb. 11, 2010

(30) Foreign Application Priority Data
Oct. 19, 2006 (EP) ..................................... 06021936

(51) Int. Cl.
| C07K 7/00 | (2006.01) |
| C07K 11/00 | (2006.01) |
| C12Q 1/00 | (2006.01) |
| A61K 38/00 | (2006.01) |
| A61K 39/00 | (2006.01) |
| C07K 16/12 | (2006.01) |
| A61K 39/02 | (2006.01) |
| C07K 16/40 | (2006.01) |
| C12N 9/10 | (2006.01) |
| C12Q 1/48 | (2006.01) |

(52) U.S. Cl.
CPC .............. *C07K 16/121* (2013.01); *A61K 39/105* (2013.01); *C07K 16/40* (2013.01); *C12N 9/104* (2013.01); *C12Q 1/48* (2013.01); *C12Y 203/02002* (2013.01); *A61K 39/00* (2013.01); *G01N 2333/91074* (2013.01)

(58) Field of Classification Search
CPC ....... A61K 39/00; A61K 39/02; A61K 39/39; A61K 2039/6068; A61K 35/74; A61K 38/04; A61K 38/16; C07K 14/705; C07K 14/195; C12Q 1/00; C12Q 1/689; C12N 1/00; C12N 2510/00
USPC ..................... 424/184.1, 234.1, 185.1, 190.1; 435/183, 69.3, 6.15; 530/300; 514/2.3, 514/2.4
See application file for complete search history.

(56) References Cited

U.S. PATENT DOCUMENTS

| 6,380,217 B1 | 4/2002 | McGovern | |
| 2002/0160456 A1* | 10/2002 | Kleanthous et al. | 435/69.3 |
| 2007/0042448 A1* | 2/2007 | Boneca et al. | 435/7.32 |

FOREIGN PATENT DOCUMENTS

| JP | 2000-229997 A | 8/2000 |
| JP | 2003-531866 A | 10/2003 |
| JP | 2004000022 A | 1/2004 |
| JP | 2004-307477 A | 11/2004 |
| JP | 2006-505527 A | 2/2006 |
| WO | WO 98/17804 A2 * | 4/1998 |
| WO | WO0001825 A1 * | 1/2000 |
| WO | 01/82965 A1 | 11/2001 |
| WO | 2004/110362 A2 | 12/2004 |

OTHER PUBLICATIONS

Colman et al. (Research in Immunology 145: 33-36, 1994.*
Houghten et al. (New Approaches to Immunization, Vaccines 86, Cold Spring Harbor Laboratory, p. 21-25, 1986.*
Greenspan et al, Nature Biotechnology 17:936-937, 1999.*
Agarwal et al. Mayo Clin Proc 2008; 83(2):169-175.*
Unanue, Emil. In Samter's Immunological Diseases, 6th edition, 2001, chapter 6.*
Shibiyama et al. Molecular Microbiology vol. 47, issue 2, p. 443-451, 2003.*
Voland et al (Infection and Immunity, vol. 71, No. 7, p. 3837-3843, Jul. 2003).*
Phadnis et al. Infection and Immunity, Mar. 1996, p. 905-912.*
Jerry Balentine. Lymphoma. Emedicine Health.http"www.emedicinehealth.com/script/main/art.asp?articlekey=58951&pf=3&page=1. retrieved Aug. 25, 2011.*
Japanese Office Action cited in Japanese counterpart application No. JP2009-532733, dated Jan. 31, 2014. English translation provided.
Ikeda, Yoshitaka, et al. "Involvement of Ser-451 and Ser-452 in the Catalysis of Human γ-Glutamyl Transpeptidase" The Journal of Biological Chemistry. vol. 270, No. 38, Sep. 22, 1995. pp. 22223-22228. XP009078675. Cited in JPOA issued in counterpart appln. No. JP2009-532733, dated Jan. 31, 2014.
Chavalier, Catherine, et al. "Essential Role of *Helicobacter pylori* γ-glutamyitranspeptidase for the Colonization of the Gastric Mucosa of Mice" Molecular Microbiology. 1999. p. 1359-1372. Cited in JPOA issued in counterpart appln. No. JP2009-532733, dated Jan. 31, 2014.

* cited by examiner

*Primary Examiner* — Gary Nickol
*Assistant Examiner* — Mary Lyons
(74) *Attorney, Agent, or Firm* — Rossi, Kimms & McDowell LLP

(57) ABSTRACT

The present invention is related to a polypeptide comprising an amino acid sequence, whereby the amino acid sequence of the polypeptide is at least 80% identical to a stretch of consecutive amino acids of the region of HPGGT comprising an amino acid sequence corresponding to SEQ. ID. No. 1, whereby such region is defined by
(a) amino acid positions 150 to 200 of the amino acid sequence according to SEQ. ID. No. 1, or
(b) amino acid positions 410 to 480 of the amino acid sequence according to SEQ. ID. No. 1, and
whereby the polypeptide is suitable to elicit an immune response which is capable of inhibiting the catalytic activity of HPGGT.

25 Claims, 11 Drawing Sheets

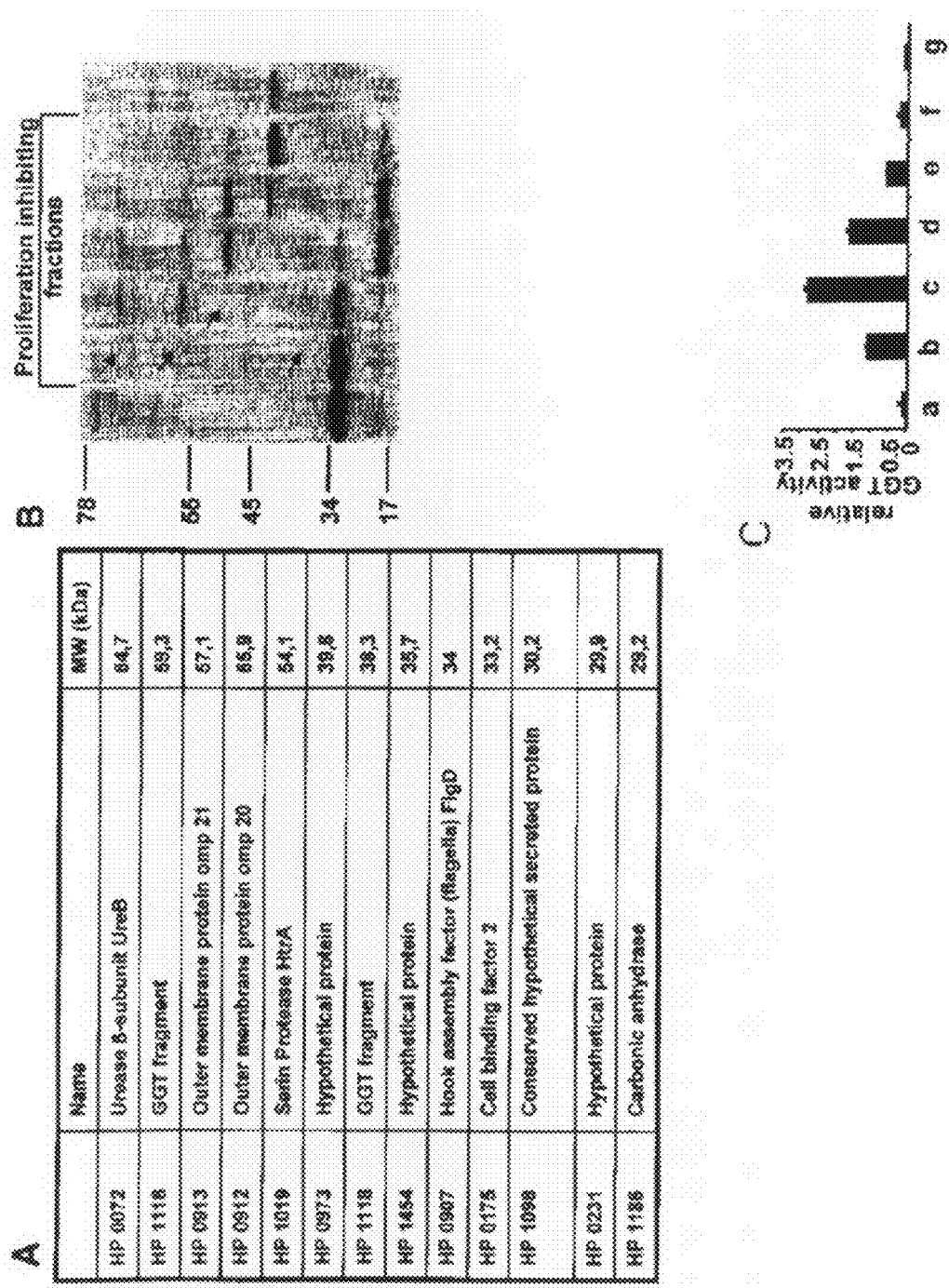
Figure 1 A-C

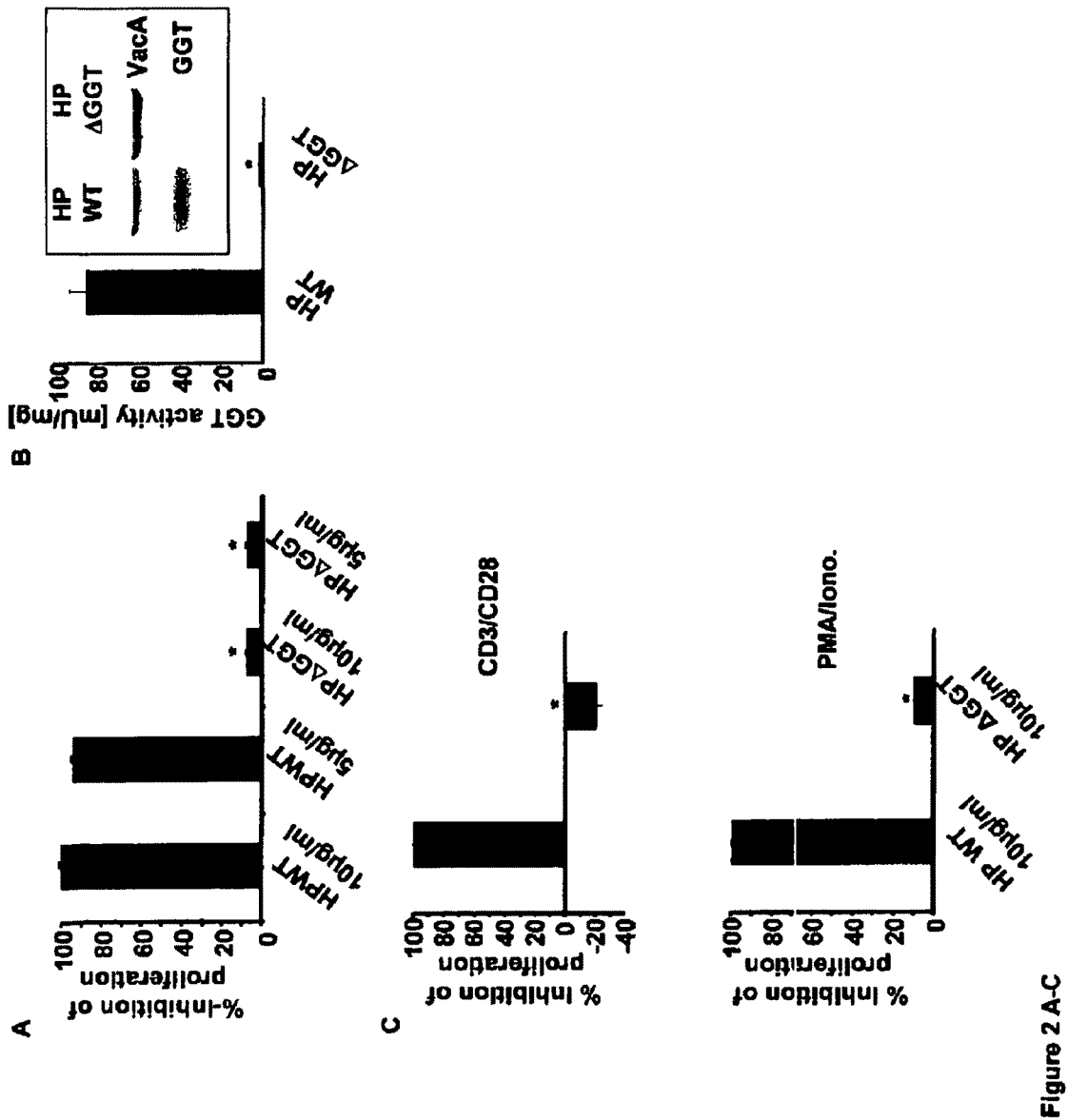
Figure 2 A-C

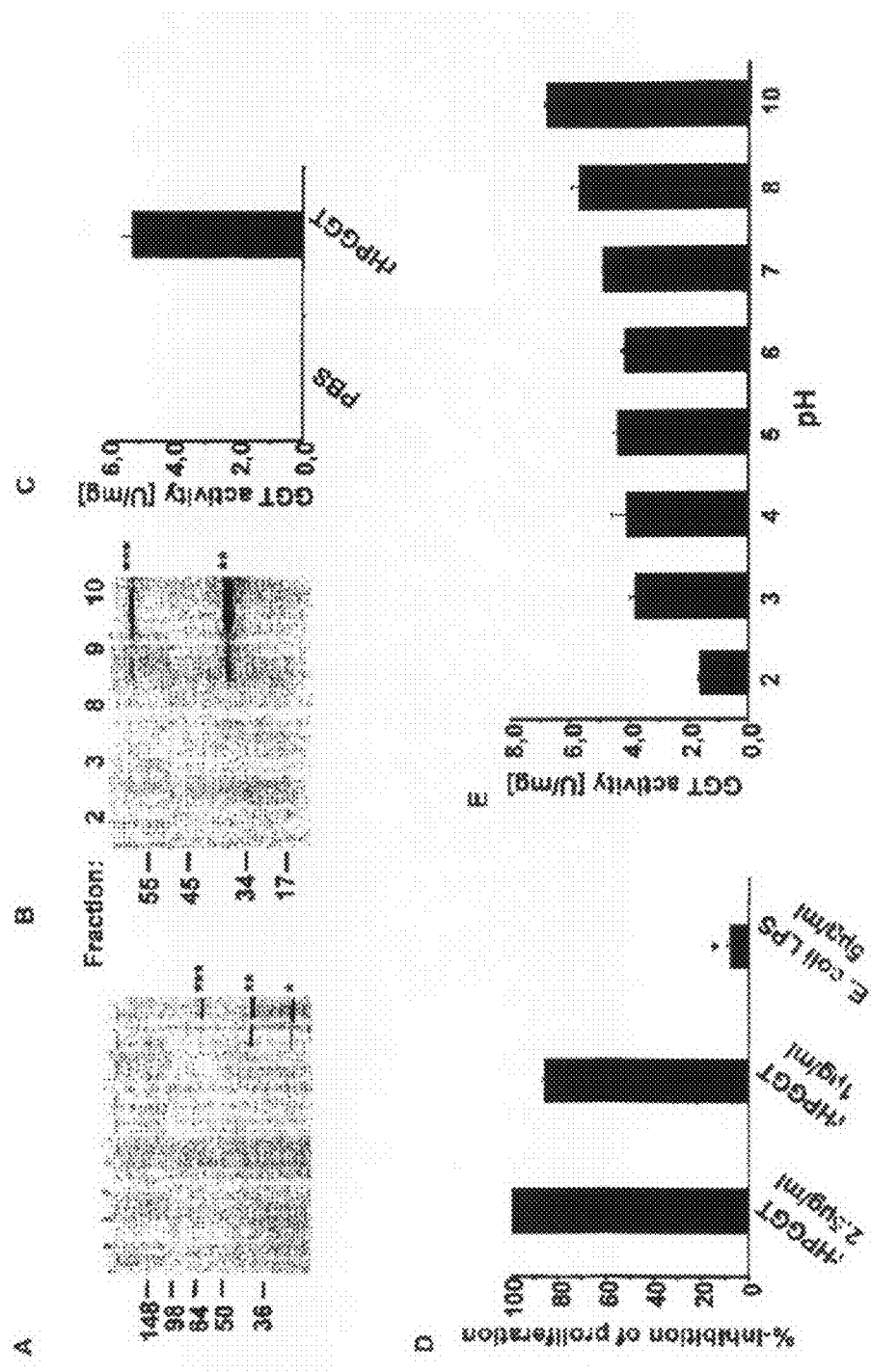
Figure 3 A-E

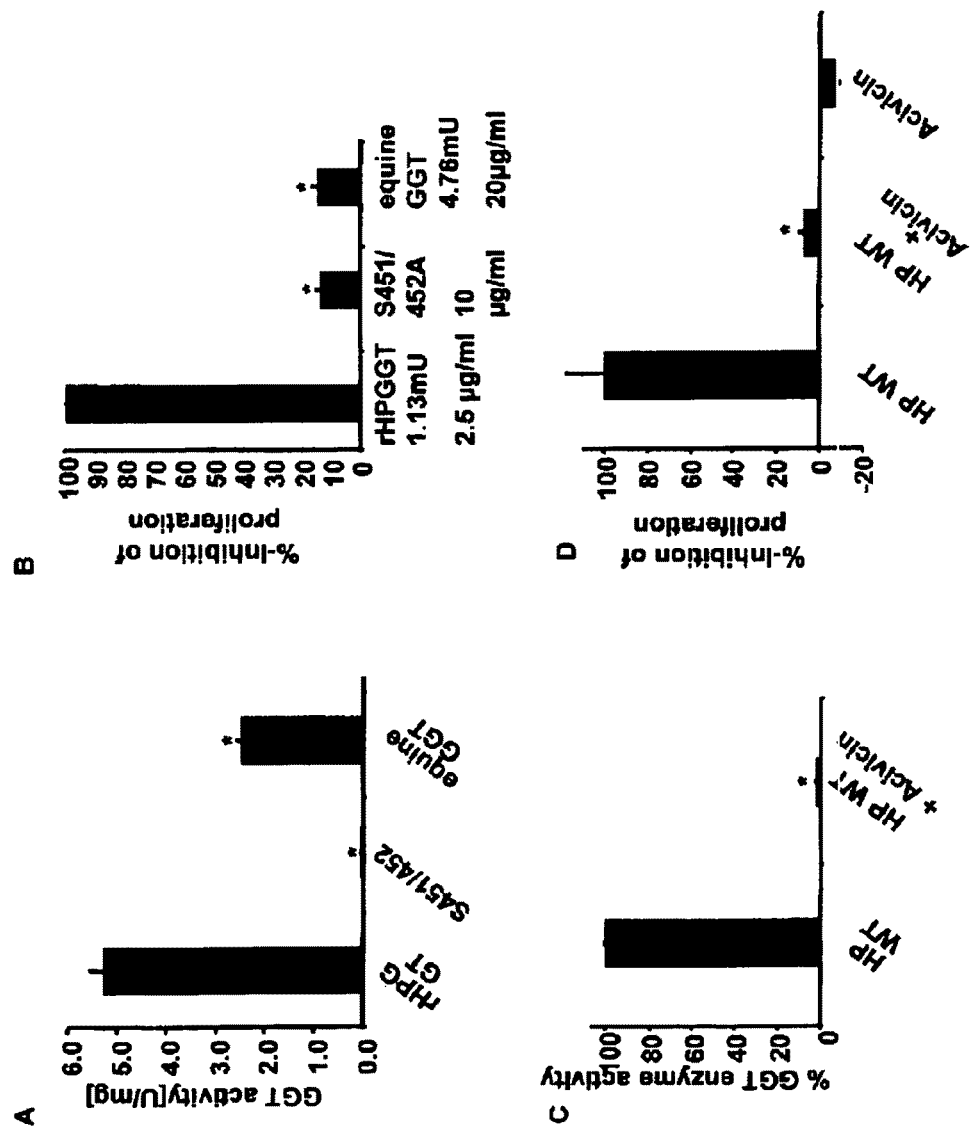
Figure 4 A-D

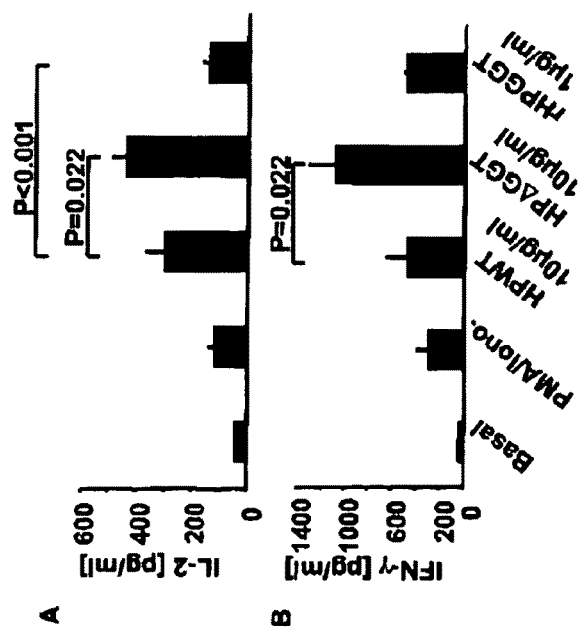
Figure 5 A-B

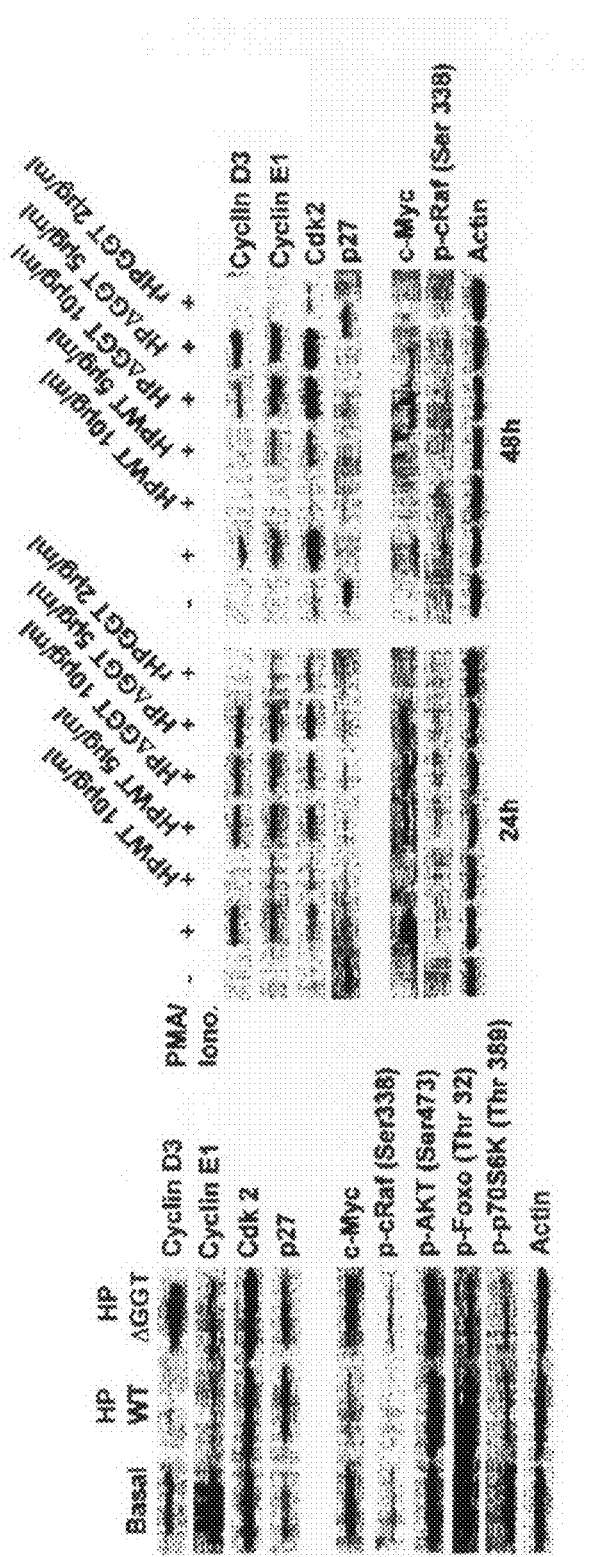
Figure 6.8

METHOD FOR TREATING *HELICOBACTER PYLORI* INFECTIONS

This is a U.S. National Phase Application of PCT International Application PCT/EP2007/009106, having an international filing date of Oct. 19, 2007, which is based on and claims priority from EP 06021936.7 filed on Oct. 19, 2006, the contents of which are incorporated herein in their entirety by reference.

The present invention is related to polypeptides which are fragments of gamma glutamyl transpeptidase of *Helicobacter pylori* (HPGGT); an immunogenic composition comprising them, an immunogenic composition comprising an inactivated form of HPGGT; the use of such polypeptides and inactive fragment of HPGGT; antibodies, aptamers, and spiegelmers directed against and specifically binding such polypeptides and inactive form of HPGGT; a method for identifying a drug candidate, a method for developing a vaccine; the use of a ligand of HPGGT.

*Helicobacter pylori* is a gram-negative pathogen that selectively colonizes the human gastric mucosa and is prevalent in more than 50% of the world population. The infection mostly persists lifelong and has been implicated in the pathogenesis of gastric and duodenal ulcers, gastric mucosa-associated lymphoid-like tissue lymphoma, and gastric cancer. A hallmark of *H. pylori* infection is chronic active gastritis, characterized by dense infiltration of the mucosa by neutrophilic granulocytes, lymphocytes, and monocytes/macrophages. Several studies have provided evidence that T-helper type 1 cells are increased and activated during *H. pylori*-associated gastritis, showing up-regulation of CD25 and CD69 in vivo. A strong humoral response to a variety of *H. pylori* antigens also is elicited. Despite this inflammatory response, the infection is not cleared by the host immune system. Therefore, it appears that *H. pylori* interferes with the immune system, but the distinct mechanism remain obscure so far.

Some studies have addressed this issue and described passive and active ways *H. pylori* escape the immune response. Resistance of *H. pylori* to phagocytosis has been reported and depends on virulence genes, such as virB7 and virB11, which encode components of the type IV secretion apparatus. Zabaleta et al reported *H. pylori* arginase to inhibit T-cell proliferation and reduce the expression of the T-cell receptor ζ chain. A proinflammatory peptide of *H pylori* has been shown to induce lymphocytic dysfunction by activating monocytes to produce reactive oxygen radicals. These data emphasize the interaction of the bacteria with the nonspecific immune response; however, a specific T-cell response appears to be decisive for elimination of the bacteria because vaccination trials have failed in mice deficient of T cells or interferon-gamma (IFN-gamma).

Despite these efforts, the reasons for the chronic persistence of the gastric pathogen remain obscure.[1] It has been shown that CD4 positive T cells are crucial for bacterial elimination[2] but are inhibited in their proliferation by *H. pylori*.[3] In this context several groups have investigated immunosuppressive effects of proteins from *H. pylori*. Knipp and co-workers partially purified a so-called "proliferation-inhibiting-protein (PIP)", which reduced the proliferation of lymphocytes and monocytes independently of the virulence factors CagA (cytotoxin associated gene A) and VacA (vacuolating cytotoxin A).[4]

In contrast, two groups recently reported that lymphocyte proliferation was suppressed in the presence of high concentrations of purified VacA.[5,6] Paradoxically however, VacA-deficient *H. pylori* mutants had no defect in their proliferation inhibiting properties.[5] In addition it has been early recognized that gastric inflammation is not altered or even increased in patients infected with VacA-expressing *Helicobacter* strains.[7,8]

It was shown earlier, that secreted products of *H. pylori* inhibited T lymphocyte proliferation by inducing a cell cycle arrest in G1 phase.[3] This effect was independent from known virulence factors including the proteins VacA and CagA.

In spite of this increasing work about the possible mechanisms of *H. pylori* to escape the elimination by the host, a substantial success in developing clinical means for specifically treating or preventing *H. pylori* infection is not yet obtained.

The problem underlying the present invention is to provide polypeptides which are suitable for eliciting an immune response in an animal or human being, whereby such immune response confers protection against *H. pylori* infection and any disease associated with or caused by *H. pylori*.

It is a further problem underlying the present invention to provide an immunogenic composition which is suitable to elicit such immune response.

Another problem underlying the present invention is to provide means for identifying novel drug candidates for treating and/or preventing a *H. pylori* infection as well as methods for treating and preventing this infection.

These and other problems are solved by the subject matter of the independent claims. Preferred embodiments maybe taken from the dependent claims.

More specifically, the problem is solved in a first aspect by a polypeptide comprising an amino acid sequence, whereby the amino acid sequence of the polypeptide is at least 80% identical to a stretch of consecutive amino acids of the region of HPGGT comprising an amino acid sequence corresponding to SEQ. ID. No. 1, whereby such region is defined by (a) amino acid positions 150 to 200 of the amino acid sequence according to SEQ. ID. No. 1, or (b) amino acid positions 410 to 480 of the amino acid sequence according to SEQ. ID. No. 1, and whereby the polypeptide is suitable to elicit an immune response which is capable of inhibiting the catalytic activity of HPGGT.

In an embodiment of the first aspect the polypeptide comprises about 15 to about 30 amino acids.

The problem is solved in a second aspect by a polypeptide, which is preferably a polypeptide according to the first aspect, whereby the polypeptide comprises an amino acid sequence corresponding to (a) amino acid positions 150 to 200 of the amino acid sequence according to SEQ. ID. No. 1, or (b) amino acid positions 410 to 480 of the amino acid sequence according to SEQ. ID. No. 1, whereby the polypeptide comprises about 15 to about 30 amino acids.

In an embodiment of the second and first aspect the amino acid sequence of the polypeptide corresponds to a stretch of 15 to 30 contiguous amino acids of said positions.

In an embodiment of the second and first aspect the polypeptide comprises a sequence selected from the group comprising

| | |
|---|---|
| QRQAETLKEARERFLKY, | (SEQ. ID. No. 2) |
| FDIKPGNPNLYGLVGGDANAI, | (SEQ. ID. No. 3) |
| DFSIKPGNPNLYGLVGGDANAIEANKRPL and | (SEQ. ID. No. 4) |
| SSMSPTIVLKNNKVFLVVGSP. | (SEQ. ID. No. 5) |

The problem is solved in a third aspect by a immunogenic composition comprising one or several of the polypeptides according to the first and the second aspect.

The problem is solved in a fourth aspect by an immunogenic composition comprising an inactivated form of HPGGT.

The problem is solved in a fifth aspect by a immunogenic composition comprising a fragment of HPGGT, whereby such fragment consists of a stretch of contiguous amino acids comprising amino acids 451 and 452 of HPGGT.

In an embodiment of the third, fourth and fifth aspect the composition is for vaccination of an animal or a human being.

In an embodiment of the third, fourth and fifth aspect the composition is capable of inducing within an animal or a human being an immune response.

In an embodiment of the third, fourth and fifth aspect the immune response is an antibody response.

In an embodiment of the third, fourth and fifth aspect the antibody response comprises antibodies with an inhibitory effect on HPGGT, more preferably on the specific activity of HPGGT and/or an abrogating effect on the HPGGT dependent suppression of lymphocyte proliferation.

In an embodiment of the third, fourth and fifth aspect the composition is for promoting activation and proliferation of lymphocytes in a patient suffering from *H. pylori* infection or being at risk of developing an infection with *H. pylori*.

In an embodiment of the third, fourth and fifth aspect the lymphocytes are B or T cells.

In an embodiment of the third, fourth and fifth aspect the composition comprises one or several adjuvants.

In an embodiment of the third, fourth and fifth aspect the composition comprises one or several antigens from *H. pylori*.

In an embodiment of the third, fourth and fifth aspect the antigen is selected from the group comprising outer membrane proteins.

In an embodiment of the third, fourth and fifth aspect the antigen is selected from the group comprising HpaA, Omp18 and combinations thereof.

In an embodiment of the third, fourth and fifth aspect the composition is for the prevention and/or the treatment of a disease caused by or associated with *H. pylori*, more preferably a disease caused by or associated with *H. pylori* infection.

In an embodiment of the third, fourth and fifth aspect the disease is selected from the group comprising infection with *H. pylori*, gastro duodenal disorders caused by *H. pylori*, gastritis, chronic gastritis, gastric or duodenal ulcer, stomach cancer and (MALT) lymphoma.

In an embodiment of the third, fourth and fifth aspect the immunogenic composition is a vaccine.

The problem underlying the present invention is solved according to sixth aspect by the use of a polypeptide according to the first aspect of the present invention for the manufacture of a medicament.

The problem underlying the present invention is solved in a seventh aspect by the use of an immunogenic composition according to the third, fourth and fifth aspect of the present invention for the manufacture of a medicament.

In an embodiment of the sixth and the seventh aspect of the present invention the medicament is a vaccine.

In an embodiment of the sixth and the seventh aspect of the present invention the medicament is for the prevention and/or the treatment of a disease caused by or associated with *H. pylori*, more preferably a disease caused by or associated with *H. pylori* infection.

The problem underlying the present invention is solved in an eighth aspect by the use of a polypeptide according to the first aspect for the detection of an antibody in a sample, whereby the antibody is directed to HPGGT.

In an embodiment of the eighth aspect the antibody is capable of inhibiting HPGGT enzymatic activity and/or inhibitory activity of HPgGT on lymphocyte proliferation.

The problem underlying the present invention is solved in a ninth aspect by an antibody specifically binding to a polypeptide according to the first aspect.

In an embodiment of ninth aspect the antibody has an inhibitory effect on HPGGT, more preferably on the specific activity of HPGGT and/or an abrogating effect on the HPGGT dependent suppression of lymphocyte suppression of lymphocyte proliferation.

The problem underlying the present invention is solved in a tenth aspect by a nucleic acid coding for the antibody according to the ninth aspect.

The problem underlying the present invention is solved in an eleventh aspect by a nucleic acid molecule specifically binding to a polypeptide according to the first aspect or binding to a fragment of HPGGT, whereby such fragment consists of a stretch of contiguous amino acids comprising amino acids 451 and 452 of HPGGT, whereby the nucleic acid molecule is selected from the group comprising aptamers and spiegelmers.

In an embodiment of the eleventh aspect the nucleic acid has an inhibitory effect on HPGGT, more preferably on the specific activity of HPGGT and/or an abrogating effect on the HPGGT dependent suppression of lymphocyte proliferation.

The problem underlying the present invention is solved in a twelfth aspect by the use of an antibody according to the ninth aspect for the manufacture of a medicament.

The problem underlying the present invention is solved in a thirteenth aspect by the use of a nucleic acid according to the eleventh aspect, for the manufacture of a medicament.

In an embodiment of the twelfth and thirteenth aspect the medicament is for the treatment and/or the prevention of a disease caused by or associated with *H. pylori*, more preferably a disease caused by or associated with *H. pylori* infection.

The problem underlying the present invention is solved in a fourteenth aspect by a method for identifying a drug candidate for the treatment of a disease comprising the steps of assessing the drug candidate's
   a. inhibitory effect on the specific activity of the gamma-glutamyl transpeptidase of *H. pylori* and
   b. abrogating effect on the HPGGT dependent suppression of lymphocyte proliferation.

In an embodiment of the fourteenth aspect the disease is caused by or associated with *H. pylori*, more preferably a disease caused by or associated with *H. pylori* infection, and more preferably *H. pylori* infection in humans.

The problem underlying the present invention is solved in a fifteenth aspect by a method for developing a vaccine comprising the steps of
   a) providing immunogenic compositions comprising HPGGT or at least one fragment thereof;
   b) immunizing animals with the immunogenic compositions and therewith generating antibodies;
   c) assessing the antibodies for their inhibitory effect on the specific activity of the gamma-glutamyl transpeptidase of *H. pylori* and their abrogating effect on the HPGGT dependent suppression of lymphocyte proliferation and
   d) selecting a suitable immunogenic composition.

In an embodiment of the fifteenth aspect the vaccine is a vaccine against a *H. pylori* infection in humans.

The problem underlying the present invention is solved in a sixteenth aspect by the use of a ligand of HPGGT for the manufacture of a drug for the prevention and/or a disease, whereby the ligand significantly inhibits the HPGGT activity and abrogates the HPGGT dependent suppression of lymphocyte proliferation.

In an embodiment of the sixteenth aspect the disease is by or associated with H. pylori, more preferably a disease caused by or associated with H. pylori infection.

In an embodiment of the sixteenth aspect the ligand is an antibody according to the ninth aspect, or a nucleic acid according to the eleventh aspect.

In an embodiment of the sixteenth aspect lymphocyte proliferation and/or activation is assessed in a lymphocyte proliferation assay.

The problem underlying the present invention is solved in a seventeenth aspect by the use of HPGGT for the manufacture of an immune suppressant composition.

The problem underlying the present invention is solved in an eighteenth aspect by an immune suppressant composition obtainable as supernatant after having incubated HPGGT and glutamine in a media enabling the HPGGT specific activity.

Without wishing to be bound by any theory the present inventor has surprisingly found that a ligand to the gamma glutamyl transpeptidase of Helicobacter pylori (HPGGT) (E.C. 2.3.2.2.) can be used for the treatment and/or prevention of H. pylori infections, in particular gastro duodenal disorders, whereby the ligand is an inhibitor of the catalytic activity of the HPGGT and restores lymphocyte proliferation compared to a control which is suppressed in the presence of this enzyme. Furthermore, the present inventor has found that when incubated together with HPGGT the lymphocyte proliferation is blocked by the HPGGT specific activity leading to G1 cell cycle arrest in the lymphocytes—and therewith inhibiting the lymphocyte proliferation. Consequently, the inhibition of the HPGGT specific activity abrogates the inhibition of the lymphocyte proliferation and in consequence makes it impossible for H. pylori to escape the immune system of the host. Thus, the use of the ligands as suggested by the present invention prevents or at least substantially reduces the H. pylori colonization within the host/patient. Finally, the present inventor has found that the catalytic activity of the gamma glutamyl transpeptidase (GGT) of H. pylori is necessary for the suppression lymphocyte proliferation, in particular T cell proliferation within the host. This was clearly evidenced by showing that mutant bacteria deficient in GGT activity lost the ability to abrogate proliferation of lymphocytes, and at the same time were unable to colonize mice. The inhibitory effect on lymphocytes was fully present with recombinant HPGGT. The analysis of its effects on signal transduction in T cells suggests a disruption of the Ras signaling pathway leading to induction of a G1 cell cycle arrest. It is important to note that every H. pylori strain possesses HPGGT, and targeting of this enzyme by inhibitory ligands will provide a novel therapy applicable to every H. pylori infection, thereby avoiding problems associated with antibiotic therapy (resistance, side effects, selection of mutations etc). In accordance with the present invention, preferably protection against H. pylori infection is conferred by inhibiting the catalytic activity of HPGGT and thereby breaking the immune suppression which otherwise hinders an effective immune response against H. pylori.

HPGGT is widely distributed among animals, plants and bacteria. It represents a heterodimeric protein, which is translated as a single polypeptide chain and posttranslationally cleaved into two subunits with different molecular weights. The mammalian form of the enzyme is a membrane-bound protein, which is mainly expressed on the luminal surface of glands and tubules of the whole body. Cellular localization of some bacterial GGTs including the Helicobacter pylori homologue is different from that of the mammalian enzyme. The HPGGT has been previously shown to be secreted into the extracellular medium (Bumann et al 2002). In addition, an alignment of the amino-acid sequences of different GGT homologues revealed low homology of 22% between HPGGT and the human and other mammalian GGTs but higher homology towards bacterial homologues. Another important difference between HPGGT and homologues from other species is the lack of GY-residues at the C-terminal end of the HPGGT (Chevalier et al 1999). Thus, substantial differences regarding cellular localization and protein structure between the HPGGT and its mammalian homologues are apparent.

The gamma-glutamyltransferase is also known as glutamyl transpeptidase; a-glutamyl transpeptidase; g-glutamyl peptidyltransferase; g-glutamyl transpeptidase; g-GPT; g-GT; g-GTP; L-g-glutamyl transpeptidase; L-g-glutamyltransferase; L-glutamyltransferase; GGT; g-glutamyltranspeptidase. The specific (catalytic) activity is the transfer of the glutamyl residue as outlined below:

(5-L-glutamyl)-peptide+an amino acid=peptide+5-L-glutamyl amino acid

This reaction or the capability to perform such reaction is also referred to herein as the enzymatic activity of HPGGT or the specific activity of HPGGT.

The GTT activity can be assessed with methods known to the person skilled in the art (e.g. using L-gamma-glutamyl-p-nitroanilide as donor substrate; see below). The lymphocyte proliferation assay in the presence or absence of HPGGT and/or the ligand can be conducted as described in detail herein.

GGT has been described earlier by other groups as a factor from H. pylori important for colonization in vivo.[11,13] However, the underlying cause of this observation remained obscure.

The present invention provides clear evidence for a GGT-dependent inhibition of human T lymphocyte proliferation and induction of G1 arrest by H. pylori. This was proven on the one hand by the use of isogenic GGT knock out mutants of the bacteria, which failed to suppress proliferation of anti-gen-stimulated primary human T cells as well as of PBMC. On the other hand a recombinant HPGGT expressed in E. coli inhibited T cell proliferation in the absence of other proteins secreted by H. pylori. Interestingly, our data show that mammalian GGT lacked this inhibitory effect. As mentioned above, differences in the structure and localization of mammalian and HPGGT have been reported. Our results point towards further distinctions in the catalytic mechanisms and/or the substrate specificity of mammalian and HPGGT being responsible for the inability of mammalian GGT to inhibit the proliferation of lymphocytes.

Structural studies and mutagenesis experiments have been used to identify serine residues 451 and 452 as essential for catalytic activity of the GGT.[21] It is shown herein that site-directed mutagenesis of serine 451/452 of HPGGT to alanine results in a complete abrogation of its catalytic and particularly its inhibitory activity towards lymphocytes which is in contrast to the technical teaching of the prior art where amino acid position 380 (T380) is reported as being crucial for the catalytic activity of HPGGT[31]. Accordingly, incubation of the HPGGT with the GGT inhibitor acivicin completely abolishes the catalytic activity as well as the inhibitory effect of the enzyme. Thus, our data demonstrate that the structural integrity of the catalytic domain of HPGGT is a necessary prerequisite for its immunosuppressive effect. In line with an important role of GGT from *H. pylori* during colonization in vivo[11,13], we found that this enzyme is catalytically active even at the low pH values present in the gastric mucosa of the host.

It is well established that epithelial cells in the human stomach form a continuous barrier which restricts the movement of molecules between the internal and external compartments. In addition passive diffusion of macromolecules through the paracellular space of this barrier is prevented by various mechanisms including tight and adherens junctions. Thus, the question arises how the GGT protein secreted by *Helicobacter pylori* could interact with the immune system of the host on the other side of the epithelial barrier to suppress T cell proliferation. In this context it has been demonstrated previously that HP is able to weaken the barrier function of the gastric epithelium by several mechanisms. In addition the disruption of epithelial junctional complexes by HP proteins VacA and CagA as well as increased transcytotic protein transport across the epithelial barrier induced by *H. pylori* urease has been demonstrated before. These mechanisms finally lead to the increased presence of HP proteins in the lamina propria and their interaction with cells of the immune system infiltrating the gastric mucosa as a result of *H. pylori* infection. In support of an affection of T cells in the gastric mucosa by the HPGGT our results show a pronounced serum antibody response towards this virulence factor in HP infected but not in uninfected control patients. This supports the notion of an antigenic processing of GGT protein components and presentation of these antigens to components of the immune system including T lymphocytes in the gastric mucosa. Thus, suppression of T lymphocyte proliferation in the gastric mucosa via HPGGT might contribute to immune evasive mechanisms of *Helicobacter pylori* facilitating its chronic persistence in the human stomach.

The results of the research underlying the instant invention reveal that important mechanisms of T cell activation are intact during incubation with *H. pylori* wild-type supernatants and also with recombinant HPGGT. This is in line with a previous study of the present inventor showing that expression of the cell surface antigens CD69 and CD25 (IL-2 receptor α-chain) were not reduced in the presence of *H. pylori* supernatants.[3] In addition, it is demonstrated that the suppressive influence of HPGGT on lymphocytes is mediated by an apoptosis-independent mechanism as exposure of phosphatidylserine, measured by Annexin V-FITC staining, was not increased in the presence of *H. pylori* supernatants and recombinant HPGGT. It has been described earlier that HPGGT induces oxidative stress and apoptosis in gastric epithelial cells.[12,16] The effect of the enzyme on cells of the immune system, however, was not determined previously, and the differences observed may reflect differences between the target cells.

The present inventor analyzed interference of HPGGT with cell cycle progression in T cells and found that HPGGT inhibits proliferation of lymphocytes by causing an arrest in the G1 phase of the cell cycle. The G1 arrest was characterized by increased amounts of the Cdk-inhibitor p27 as well as reduced cellular levels of Cyclin proteins. Ras- and PI3K-dependent pathways are of central importance during induction, synthesis and assembly of D-type Cyclins with their catalytic partners.[22,23] Activation of Ras-signaling induces Cyclin D-transcription through a protein cascade involving c-Raf and other kinases.[24] In addition, it is established that induction of Ras signaling leads to enhanced synthesis of c-Myc protein[25] which plays an important role during regulation of cell-cycle, cell growth, and transformation.[26] Previous studies demonstrated that PI3K-signaling proceeds independent of Ras-signaling in T cells.[17] Whereas the activation status of important mediators of PI3K-signaling (AKT, p70S6K and Foxo3) was unchanged in the presence of HPGGT, we found reduced levels of c-Raf phosphorylation and c-Myc protein in cells incubated with HPGGT. Thus, our data suggest that disruption of Ras- but not PI3K-dependent signalling by GGT from *H. pylori* plays a role during induction of a cell cycle arrest in T cells leading to abrogated cell proliferation.

Another important question is how an enzyme like the HPGGT can influence intracellular signaling events leading to cell cycle arrest and inhibition of proliferation. During the transpeptidation reaction, GGT catalyzes the transfer of a γ-glutamyl moiety from a donor to an acceptor substrate.[27] By systematic amino acid depletion analyses the present inventor found that the inhibitory effect of the HPGGT was completely abolished in the absence of the amino acid glutamine from the medium, suggesting that the inhibitory effect of GGT from *H. pylori* is mediated indirectly by the formation of metabolites during transpeptidation. This is supported by our observation that preincubation of culture medium with HPGGT and subsequent inactivation of the enzyme prior to addition to the cells is sufficient for inhibition of lymphocyte proliferation.

Previous studies described several factors of *H. pylori* distinct from GGT, which inhibited proliferation of human T lymphocytes. Wang and co-workers showed that *H. pylori* at an MOI of 300 (300 bacteria per T cell) inhibited proliferation of T cells by induction of apoptosis. However, it might be questionable whether such high amounts of bacteria come into contact with T cells in the lamina propria of the human stomach. In our previous publication (Gastroenterology 2005 2005; 128(5):1327-39) the present inventor showed that even a 300-times lower MOI of 1 (1 bacteria per T cell) was sufficient to inhibit lymphocyte proliferation in our system. When the concentration of HP culture supernatants incubated with lymphocytes was raised above 100 μg/ml apoptosis was observed in comparable amounts as Wang et al. This suggests that the inhibitory effect of HP towards lymphocytes described herein is more pronounced as and different from the mechanisms described by this group.

Another study by Zabaleta et al described the inhibition of T cell proliferation by the cytoplasmatic HP protein arginase[30]. The authors used whole cell lysates from HP containing cytoplasmatic and membrane-bound proteins of the bacteria. In contrast the present inventor used culture supernatants from HP containing its secreted proteins. Since arginase is not secreted by HP possible inhibitory effects of this enzyme towards T cells could not be detected in the system used here and are unlikely to occur in vivo.

A work by Gebert et al suggested that vacuolating cytotoxin A (VacA) secreted by *H. pylori* inhibited proliferation of T cells. The authors used bacterial supernatants at a 25-times higher concentration (250 μg/ml) than we did in our present work (10 μg/ml). In a previous study the present inventor demonstrated that high concentrations of HP culture supernatant (100 μg/ml) induced significant amount of apoptosis in lymphocytes. In addition, the presence or absence of VacA had no influence on the inhibitory effect of HP towards lymphocytes in our system (Gastro 2005).

Thus, in spite of other ways of T cell inhibition by *H. pylori* described previously, GGT secreted by the bacteria is necessary and sufficient to inhibit T cell proliferation in the system which was used here.

In summary, data underlying the present application provide a novel mechanism for immune evasion applied by *H.*

*pylori*, making use of a secreted protein to inhibit cell cycle progression of immune effector cells. It is shown that the enzyme GGT is responsible for inhibition of T cell proliferation by *H. pylori*, as the inhibitory effect was completely abolished in GGT-deficient mutants of the bacteria. This effect depended clearly on the catalytic activity of GGT, as enzymatically inactive mutants of recombinant HPGGT protein lacked the ability to suppress T cell proliferation. In addition, it is shown that a cell cycle arrest in the G1 phase of T cells was induced only in the presence of GGT from *H. pylori*. Again without wishing to be bound by any theory, further results point towards the disruption of Ras- but not PI3K-dependent signaling by HPGGT as the cause of the G1 arrest and suppressed T cell proliferation. The identification of HPGGT as a lymphocyte inhibiting factor forms the biological basis for observations in animal models, showing an important role of HPGGT for *H. pylori* colonization. The HPGGT and its possible role in the colonization of the host are discussed within the WO 00/01825 and WO98/17804. Both documents, however, do not present evidence that the HPGGT activity is responsible for the suppression of the host's immune system and they are silent on the impact of the HPGGT on the T cell proliferation and immune suppression within the host.

The present inventor has found that not only HPGGT as such, preferable the wildtype HPGGT having the amino acid sequence according to SEQ. ID. No. 1, may be used as an antigen for the generation of antibodies, aptamers, and spiegelmers, each preferably specifically binding thereto, which are suitable to inhibit the specific activity of HPGGT and/or an abrogating effect on the HPGGT dependent suppression of lymphocyte suppression of lymphocyte proliferation, but also distinct fragments thereof.

Accordingly, in one aspect the present invention is related to specific polypeptides. Such polypeptides comprise a sequence of amino acids which is identical to or corresponds to a part or stretch of amino acids of distinct regions of HPGGT. Preferably the amino acid sequence of HPGGT comprises the amino acid sequence according to SEQ. ID. No. 1.

As preferably used herein an amino acid sequence is identical to another amino acid sequence if the sequence or order of the amino acids is the same in terms of both the nature of the amino acids and their relative positioning to each other. In another embodiment, the primary amino acid sequence of the sequence which are identical, is the same.

As preferably used herein an amino acid sequence is identical to another amino acid sequence if the sequence or order of the amino acids is the same in terms of both the nature of the amino acids and their relative positioning to each other. In another embodiment, the primary amino acid sequence of the sequences which correspond to each other is the same, whereby the overall context of both corresponding amino acid sequences is either the same or is different. The overall context of an amino acid is defined by the amino acid(s) flanking one or both ends of the amino acid sequence.

It will be acknowledged by the person skilled in the art that the sequences which are identical or which correspond to each other have a sequence homology of at least 80%, 85%, 90%, 95% or 100%.

In an embodiment the polypeptide according to the present invention comprises or consists of an amino acid sequence which is identical to or corresponds to a stretch of consecutive amino acids of HPGGT. Preferably, and applicable to any embodiment and aspect of the instant invention, HPGGT has an amino acid sequence according to SEQ. ID. No. 1. It will be acknowledged by the person skilled in the art that there may exist variants and mutations of HPGGT which shall be comprised by the term HPGGT. It is also within the present invention that if the sequence of HPGGT is different from the one of HPGGT as specified in SEQ. ID. No. 1, what is disclosed herein in connection with HPGGT having the amino acid sequence as specified in SEQ. ID. No. 1 is applicable to such different form of HPGGT, too. More specifically, the person skilled in the art will identify the amino acid(s) in such different form which corresponds in its position, chemical nature and/or function to the one identified and addresses, respectively, in HPGGT having the amino acid sequence as specified in SEQ. ID. No. 1.

As disclosed herein, the polypeptide according to the instant application is identical to or corresponds to the amino acid sequence of distinct regions of HPGGT. In one embodiment such region is the region defined by amino acid positions 150 to 200 of the amino acid sequence according to SEQ. ID. No. 1. In another embodiment such region is the region defined by amino acid positions 410 to 480 of the amino acid sequence according to SEQ. ID: No. 1.

The present inventor has surprisingly found that the part of HPGGT defined by amino acids 150 to 200, and the part of HPGGT defined by amino acids 410 to 480 is particularly advantageous for being used as an antigen or a vaccine for the generation of antibodies which are capable of inhibiting the catalytic activity of HPGGT thus providing the prerequisite that an immune response is elicited against *H. pylori*, or at least HPGGT, in an organism which is infected or at risk of being infected by *H. pylori*.

Without wishing to be bound by any theory the present inventor assumes that both the region as defined by amino acid positions 150 to 200 and amino acid positions 410 to 480 have a particular relationship with the enzymatic activity of HPGGT. More specifically, the region of HPGGT as defined by amino acid positions 410 to 480 is said to be related or close to the active centre of HPGGT. More specifically, this region of HPGGT comprises the loop region in direct contact with the active centre and part of the active centre itself. Thus the blocking of this part of HPGGT is a suitable means to inhibit the enzymatic activity of HPGGT, presumably by blocking the entry of the substrate(s) of the catalytic activity of HPGGT. The same is, in principle, also true for the region of HPGGT as defined by amino acid positions 150 to 200. This region of amino acid positions 150 to 200 of HPGGT according to SEQ. ID. No. 1 is related to or forms (part of) the loop outside of the active centre of HPGGT, however is in close spatial proximity to the binding pocket for the substrate. In view of this, any molecule which specifically interferes with these regions is an agent which can be used as outlined herein in more detail in connection with the an antibody having this kind of binding characteristics. Apart from antibodies, peptide aptamers, anticalines, aptamers and spiegelmer as described in the prior art can be generated and used, respectively, for the various purposes disclosed herein for antibodies.

The instant application this provides polypeptides the sequence of which corresponds or is identical to the following amino acid positions:

(a) (150+n) to (150+n+m), whereby n is any integer from 0 to 35 and m is any integer from 15 to 30. It will be understood that the position thus defined are those which result from any combination of n and m. It will further be understood that such combination is preferably limited insofar that the upper position which is thus defined is about 200; the position defined by (150+n) is also referred to as the lower position; and the position defined by (150+n+m) is also referred to as the upper position.

(b) (410+n) to (410+n+m), whereby n is any integer from 0 to 55 and m is any integer from 15 to 30. It will be understood that the position thus defined are those which result from any combination of n and m. It will further be understood that such combination is preferably limited insofar that the upper position which is thus defined is about 200; the position defined by (410+n) is also referred to as the lower position; and the position defined by (410+n+m) is also referred to as the upper position.

In a further embodiment the polypeptides according to the present invention are fragments of HPGGT, preferably immunogenic fragments of HPGGT and more preferably immunogenic fragments of HPGGT which are suitable to elicit an immune response in host organisms, preferably an antibody response, whereby the antibody has an inhibitory effect on HPGGT, more preferably on the specific activity of HPGGT and/or an abrogating effect on the HPGGT dependent suppression of lymphocyte proliferation. Preferably the immunogenic fragment according to the invention comprises the amino acids 451 and or 452 of the HPGGT. The fragment can be of any length. However, peptides of 10 to about 50 amino acid residues, more preferred 10 to 40, 10 to 30, or most preferred 10 to 20 are used. Epitope prediction algorithms for peptide-based vaccine design are applied here. As preferably used herein a host organism is an animal, preferably a mammal, or a human being which, preferably, are capable of developing an immune response against an antigen.

As preferably used herein, an amino acid is an alpha-amino acid. As also preferably used herein, an amino acid is either a D- or an L-amino acid, preferably an L-amino acid. Still preferably an amino acid is a naturally occurring amino acid.

The present inventor has also surprisingly found that mutagenesis from serine residues 451 and/or 452 to alanine of the HPGGT completely abolished the enzymatic activity of recombinant HPGGT and abrogated its inhibition of the T cell proliferation. However, the substitution of the serine residue 385 (S385A) did not reduce the HPGGT dependent inhibitory effect on T cell proliferation, although the catalytic activity of this mutant HPGGT was significantly (i.e. for about 50%) lowered. Accordingly, a suitable drug substance for the treatment of *H. pylori* infection needs to fulfill two requirements, namely (i) it has to exhibit an inhibitory effect on the catalytic activity of HPGGT and furthermore has to restore the T cell proliferation when incubated with HPGGT. The effective method according to the invention for the identification of suitable drug candidates consequently comprises both assessments.

In the lights of this finding another aspect of the present invention is related to the use of an inactivated form of HPGGT.

An inactivated form of HPGGT is in an embodiment a HPGGT which is lacking the enzymatic activity of HPGGT as indicated herein. It will be acknowledged by the persons skilled in the art that there are various ways to provide for such inactivated form of HPGGT, including deletions of one or several amino acids, alteration of one or more amino acid, always compared to the enzymatically active HPGGT. One embodiment of an inactivated form of HPGGT is the one which is lacking the serine amino acids at positions 451 and 452 of the amino acid sequence according to SEQ. ID. No. 1. In an embodiment the inactivated form of HPGGT is still able to elicit an immune response as described herein, preferably an antibody response in an animal and/or a human being which comprises antibodies with an inhibitory effect on wild type HPGGT, more preferably on the specific activity of HPGGT and/or an abrogating effect on the HPGGT dependent suppression of lymphocyte proliferation. As preferably use herein the term specific activity of HPGGT is used in a synonymous manner to enzymatic activity and more specifically the enzymatic activity of HPGGT as described herein. A further embodiment of an inactivate form of HPGGT is a HPGGT having the wildtype amino acid sequence but the enzymatic effect is suppressed by the addition of an inhibitor to the enzymatic activity of HPGGT. Such inhibitor may be an antibody, spiegelmer, aptamer or any molecule depriving HPGGT of factors including ions needed for the enzymatic activity of HPGGT.

It will be understood that the polypeptides, the inactivated forms of HPGGT and HPGGT are also referred to herein as target molecules, particularly in connection with the generation of antibodies, aptamers and spiegelmers specifically binding thereto.

A further aspect of the present invention is related to antibodies directed against the polypeptides according to the present invention, the inactivate forms of HPGGT or HPGGT, preferably HPGGT as of the wild type which typically has the amino acid sequence according to SEQ. ID. No. 1.

Antibodies are preferably used herein comprise both monoclonal antibodies and polyclonal antibodies, the manufacture and generation, respectively, which is well known to the one skilled in the art.

The manufacture of an antibody specific for the target is known to the person skilled in the art and, for example, described in Harlow, E., and Lane, D., "Antibodies: A Laboratory Manual," Cold Spring Harbor Laboratory, Cold Spring Harbor, N.Y., (1988). Preferably, monoclonal antibodies may be used in connection with the present invention, which may be manufactured according to the protocol of Köhler and Milstein and further developments based thereon.

Antibodies as used herein, include, but are not limited to, complete antibodies, antibody fragments or derivatives such as Fab fragments, Fc fragments and single-stranded antibodies, or anticalins, as long as they are suitable and capable of binding to the target. Apart from monoclonal antibodies also polyclonal antibodies may be used and/or generated. The generation of polyclonal antibodies is also known to the one skilled in the art and, for example, described in Harlow, E., and Lane, D., "Antibodies: A Laboratory Manual," Cold Spring Harbor Laboratory, Cold Spring Harbor, N.Y., (1988). Preferably, the antibodies used for therapeutic purposes are humanized or human antibodies.

The antibodies, which may be used according to the present invention, may have one or several markers or labels. Such markers or labels may be useful for detecting the antibody either in its diagnostic application or its therapeutic application. Preferably the markers and labels are selected from the group comprising avidin, streptavidin, biotin, gold and fluorescein and used, e.g., in ELISA methods. These and further markers as well as methods are, e.g. described in Harlow, E., and Lane, D., "Antibodies: A Laboratory Manual," Cold Spring Harbor Laboratory, Cold Spring Harbor, N.Y., (1988). Additionally or alternatively, the antibodies as well as any other target antagonist or interaction partner described herein may be a labelled antagonist as more generally described herein.

It is also within the present invention that the label or marker exhibits an additional function apart from detection, such as interaction with other molecules. Such interaction may be, e.g., specific interaction with other compounds. These other compounds may either be those inherent to the system where the antibody is used such as the human or animal body or to the sample which is analysed by using the respective antibody. Appropriate markers may, for example, be biotin or fluoresceine with the specific interaction partners thereof such as avidin and streptavidin and the like being present on the respective compound or structure to interact with the thus marked or labelled antibody. Again this applies also to the other target interaction partners described herein such as aptamers and spiegelmers.

In an embodiment the antibody is an antibody, preferably a monoclonal antibody, with a specific activity against an epitope of HPGGT comprising the amino acids 451 and/or 452 of the recombinant HPGGT. In another embodiment the antibody will be targeting an epitope spatially close to these amino acid positions, preferably targeting and specifically binding to a loop adjacent to said positions, more preferably the epitopes are defined by or contained in the stretch of HPGGT defined by amino acid positions 150 to 200 of HPGGT of SEQ: ID. No. 1, more preferably positions 174-190, or by amino acid positions 410 to 480 of HPGGT of SEQ: ID. No. 1, more preferably positions 423 to 443, and derivatives thereof under the proviso that they show in essentially identical immune reactivity.

Preferably the antibodies of the invention inhibit the HPGGT specific activity and suppress the HPGGT dependent inhibition of the lymphocyte proliferation within the host by at least 50%, more preferred by at least 70%, most preferred by at least 80 or 90%. Also preferably, the antibodies according to the present invention furthermore exhibit an inhibitory effect on the HPGGT specific activity and abrogate the HPGGT dependent suppression of T cell proliferation as assessed in vitro.

Another class of interaction partners which can be used in accordance with the present invention in a way identical to the antibodies, and thus for the same purposes, are the so-called "anticalines", which are a particular form of target binding polypeptides. Anticalines and their method of manufacture are, among others, described in German patent application DE 197 42 706.

A further class of molecules which can be used in a way identical to the antibodies, and thus for the same purposes, are the so-called peptide-aptamers. Using a target, peptide aptamers can be generated using a screening process making use of a polypeptide library as described herein in more detail. The selection criterion is that the selected polypeptide is actually and specifically binding to the target.

More specifically, such peptide aptamers may be generated by using methods according to the state of the art such as phage display. Basically, a library of peptide is generated, such as in the form of phages, and this kind of library is contacted with the target molecule. Those peptides binding to the target molecule are subsequently removed from the respective reaction, preferably as a complex with the target molecule. It is known to the one skilled in the art that the binding characteristics, at least to a certain extent, depend on the particularly realized experimental set-up such as salt concentration and the like. After separating those polypeptides binding to the target molecule with a higher affinity or a bigger force, from the non-binding members of the library, and optionally also after removal of the target molecule from the complex of target molecule and polypeptide, the respective polypeptide(s) may subsequently be characterised. Prior to the characterisation optionally an amplification step is realized such as, e.g., by propagating the polypeptide coding phages. The characterisation preferably comprises the sequencing of the target binding polypeptides and ultimately of those polypeptides acting as antagonists or interaction partners of the target as defined herein. Basically, the polypeptides are not limited in their length, however, preferably polypeptides having a length from about 8 to 20 amino acids are preferably obtained in the respective methods. The size of the libraries may be about $10^2$ to $10^{18}$, preferably $10^8$ to $10^{15}$ different polypeptides, however, is not limited thereto.

A further aspect of the present invention is related to aptamers directed against the polypeptides according to the present invention, the inactivate forms of HPGGT or HPGGT, preferably HPGGT as of the wildtype which typically has the amino acid sequence according to SEQ. ID. No. 1.

Aptamers are D-nucleic acids which are either single stranded or double stranded and which specifically interact with the target molecule. The manufacture or selection of aptamers is, e.g., described in European patent EP 0 533 838. Basically the following steps are realized. First, a mixture of nucleic acids, i.e. potential aptamers, is provided whereby each nucleic acid typically comprises a segment of several, preferably at least eight subsequent randomised nucleotides. This mixture is subsequently contacted with the target molecule, whereby the nucleic acid(s) bind to the target molecule, such as based on an increased affinity towards the target or with a bigger force thereto, compared to the candidate mixture. The binding nucleic acid(s) are/is subsequently separated from the remainder of the mixture. Optionally, the thus obtained nucleic acid(s) is amplified using, e.g. polymerase chain reaction. These steps may be repeated several times giving at the end a mixture of nucleic acids having an increased ratio of nucleic acids specifically binding to the target from which the final binding nucleic acid is then optionally selected. These specifically binding nucleic acid(s) are referred to aptamers. It is obvious that at any stage of the method for the generation or identification of the aptamers samples of the mixture of individual nucleic acids may be taken to determine the sequence thereof using standard techniques. It is within the present invention that the aptamers may be stabilized such as, e.g., by introducing defined chemical groups which are known to the one skilled in the art of generating aptamers. Such modification may for example reside in the introduction of an amino group at the 2'-position of the sugar moiety of the nucleotides. Aptamers are currently used as both therapeutic and diagnostic agents. However, it is also within the present invention that the thus selected or generated aptamers may be used for target validation and/or as lead substance for the development of medicaments, preferably of medicaments based on small molecules. This is actually done by a competition assay whereby the specific interaction between the target molecule and the aptamer is inhibited by a candidate drug whereby upon replacement of the aptamer from the complex of target and aptamer it may be assumed that the respective drug candidate allows a specific inhibition of the interaction between target and aptamer, and if the interaction is specific, said candidate drug will, at least in principle, be suitable to block the target and thus decrease its biological availability or activity in a respective system comprising such target. The thus obtained small molecule may then be subject to further derivatisation and modification to optimise its physical, chemical, biological and/or medical characteristics such as toxicity, specificity, biodegradability and bioavailability.

A further aspect of the present invention is related to spiegelmers directed against the polypeptides according to the present invention, the inactivate forms of HPGGT or HPGGT, preferably HPGGT as of the wildtype which typically has the amino acid sequence according to SEQ. ID. No. 1.

Spiegelmers are a special form of aptamers. The generation or manufacture of spiegelmers which may be used or generated according to the present invention using the target is based on a similar principle. The manufacture of Spiegelmers is described in the international patent application WO 98/08856. Spiegelmers are L-nucleic acids, which means that they are composed of L-nucleotides rather than aptamers which are composed of D-nucleotides as aptamers are. Spiegelmers are characterized by the fact that they have a very high stability in biological system and, comparable to aptamers, specifically interact with the target molecule against which they are directed. In the purpose of generating Spiegelmers, a heterogenous population of D-nucleic acids is created and this population is contacted with the optical antipode of the target molecule, in the present case for example with the D-enantiomer of the naturally occurring L-enantiomer of the target. Subsequently, those D-nucleic acids are separated which do not interact with the optical antipode of the target molecule. However, those D-nucleic acids interacting with the optical antipode of the target molecule are separated, optionally determined and/or sequenced and subsequently the corresponding L-nucleic acids are synthesized based on the nucleic acid sequence information obtained from the D-nucleic acids. These L-nucleic acids which are identical in terms of sequence with the aforementioned D-nucleic acids interacting with the optical antipode of the target molecule, will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

In a further aspect the present invention is related to an immunogenic composition. The immunogenic composition comprises at least one of the polypeptides according to the present invention and/or an inactive form of HPGGT, particularly an inactive form of HPGGT as described herein, and/or wildtype HPGGT. It will be understood that said polypeptides according to the present invention and/or said inactive form of HPGGT, particularly an inactive form of HPGGT as described herein, and/or said wildtype HPGGT are, in an embodiment, conjugated to a carrier material such as KLH or Keyhole limpet hemocyanin, BSA, Ovalbumin, etc in order to present the respective antigen to the immune system of the host in a way which allows or promotes the eliciting of an immune response and elicit high titre antibodies.

It will be understood that in connection with the instant invention the immunogenic composition can be used in vitro or in vivo. In the latter case such immunogenic composition is typically a vaccine and preferably formulated as such vaccine. The immunogenic composition, and medicament and vaccine, respectively, comprising the same can be used for prevention of *H. pylori* infection, preferably in children, or for the treatment and/or prevention of animals and human beings suffering or being at risk of suffering from *H. pylori* infection and any disease caused by or associated with such organism.

In an embodiment, the immunogenic composition of the present invention comprises one or several adjuvants. Preferably adjuvants are agents which provide for a generalized stimulation of the immune system. Adjuvants are known in the art and include, but are not limited to, polycationic polymers, immunostimulatory deoxynucleotides (ODNs), synthetic KLK peptides, neuroactive compounds, alumn, Freund's complete or incomplete adjuvants, cholera toxin. Preferably the polycationic polymer is a polycationic peptide and/or whereby the neuroactive compound is human growth hormone.

In a further embodiment the immunogenic composition comprises outer membrane proteins of *H. pylori* such as BabA, HpaA, Omp 18 and a combination thereof. HpaA and Omp18 are, e.g. described in Voland p. et al., Infection and Immunity, July 2003, p. 3837-3843. It is within the present invention that the terms Bab A, Hpa A and Omp 18 comprises not only the full length polypeptide, but also any immunogenic fragment or peptide thereof. HpaA is a putative N-acetylneuraminyllactose-binding hemagglutinin, Bab A is an adhesion protein binding to Lewis blood group antigens. It will be understood that other antigens and preferably proteins and polypeptides, and respective fragments thereof, may be used for increasing the immune response against *H. pylori*. Preferred proteins and polypeptides, respectively, which may be used in an embodiment of the present invention are outer membrane proteins which are typically incorporated into the outer plasma membrane of *H. pylori* and are important for, e.g., ion transport, adherence, structural and osmotic stability and bacterial virulence.

Further antigens which may be taken from *H. pylori* and which may be part of the immunogenic composition according to the present invention, are those described in published US patent application 20070042448.

It will be acknowledged that the polypeptides and proteins of the present invention, including the inactive forms of HPGGT and the wildtype HPGGT, as well as any other compound described herein intended for administration to the animal or human body are preferably formulated. Such formulation are known to the person skilled in the art. In an embodiment the formulation is one as described in U.S. Pat. No. 6,838,089. The formulation described in this US patent is a delivery system comprising a plurality of polymer particles, wherein a water-insoluble protein antigen is incorporated with the polymer particles, the polymer particles comprising a matrix polymer which comprises one or more homo- and/or copolymers, wherein the method comprises: (a) mixing an aqueous phase (W) comprising the water-insoluble agent such as a protein and one or more hydrophilic surfactants at a concentration of 0.1 to 100 times the critical micelle concentration thereof with an organic phase (O) that comprises the matrix polymer in an organic solvent, which solvent does not denature the protein antigen and wherein O is immiscible with W, to produce a W/O emulsion, wherein either W or O or both further comprise one or more stabilizing agents added prior to mixing to stabilize the W/O emulsion in the presence of the solubilizing agent(s) and promote the incorporation of the water-insoluble protein within the polymer particles during step (b); and (b) forming droplets of said W/O emulsion by dispersing the emulsion in a fluid medium, and removing said solvent from the O phase of the W/O emulsion droplets to thereby form the polymer particles incorporating the water-insoluble protein antigen.

In a further embodiment the formulation and delivery agent for the agents and compounds described herein, is a microsphere system such as those described in U.S. Pat. No. 6,372,260.

In an aspect of the present invention the polypeptides, the inactive form of HPGGT, the antibodies, spiegelmers and aptamers according to the invention, the immunogenic composition, the pharmaceutical compositions comprising any of these according to the invention are preferably used in the prevention and/or treatment of a disease which is caused by or associated with *H. pylori*, more preferably caused by *H. pylori* infection. In an embodiment the disease are gastro duodenal disorders, caused by *H. pylori* infection. In a further embodiment the disease is gastritis, most of all chronic gastritis. Since a chronic gastritis is involved in the pathogenesis of gastric or duodenal ulcer or even stomach cancer and MALT lymphoma, the method and above agents of the invention can be used to prevent theses diseases. It can also be used to treat e.g. the gastric and duodenal ulcer disease and (MALT) lymphoma. According to the invention the general term "treatment" is used—unless otherwise explicitly defined—as any form of curing, mitigating, diagnosing or preventing a pathological disorder.

In a further aspect the instant invention and with regard to its suppressing effect on the lymphocyte proliferation, in particular T cell proliferation, the HPGGT induces immune suppression in the host and thus can be applied as a novel immune suppressant. Immune suppressants can be used e.g. for reducing the risk of organ transplant rejection after transplantation or for the treatment of auto-immune diseases, such as rheumatic arthritis, Chron's disease or atopic eczema. The catalytic activity of HPGGT requires the presence of glutamine to serve as a donor/acceptor for gamma glutamyl. Thus, an immune suppressant composition comprising HPGGT preferably further comprises glutamine.

Moreover, the inventors could show that a preincubation of the cell culture medium applied for the lymphocyte proliferation assay with glutamine, leucine and histidine and the active HPGGT exhibited anti-proliferative effect on the T cells even when the HPGGT was subsequently inactivated. Thus, it was concluded that the immune suppressing effect is HPPGT dependent; however a not yet identified direct or indirect product of the enzymatic reaction is involved in the mode of action. Accordingly, one embodiment of the invention relates to an immune suppressing composition obtainable by incubating HPGGT and glutamine, leucine and histidine, preferably within a pharmaceutically acceptable incubation media and enabling the HPGGT specific reaction. The supernatant of this reaction can then be applied as a suitable immune suppressing composition. Preferably this composition comprises a glutamyl-peptide, e.g. poly-glutamyl-glutamat or glutamyl-derivates generated by transfer of glutamyl to such substrates.

It is within the present invention that the HPGGT as used in connection with this aspect is any HPGGT which has the specific enzymatic activity described herein. Insofar, the term HPGGT comprises both the wildtype HPGGT, the full length HPGGT and any derivative and more specifically any fragment thereof having this kind of enzymatic activity. Such derivates and fragments can be produced by the person skilled in the art by using methods well known in the art.

As preferably used herein, the term promoting proliferation of lymphocytes means in a preferred embodiment promoting activation and proliferation of lymphocytes.

In a further aspect the present invention is related to a method of producing HPGGT, more specifically recombinant HPGGT which is lacking the secretion sequence (signal peptide) or with a secretion sequence which is non-functional. Such HPGGT lacking a functional secretion sequence, i.e. amino acids 1-26, cleavage site between pos. 26 and 27: LSA-AS, is advantageous insofar as such HPGGT is not secreted from a host cell during production in such host cell. In connection with this aspect, the host organism is preferably a prokaryote such as E. coli, however, is not limited thereto.

The person skilled in the art is aware of methods to prepare such HPGGT lacking a functional secretion sequence. For example, this can be accomplished by expressing a gene encoding a protein without secretory leader sequence. Such a modified HPGGT protein will remain in its host cell and thus can be purified therefrom.

In a further aspect the present invention is related to the use of the polypeptides according to the present invention and the inactive HPGGT according to the present invention for the preparation of antibodies. In a closely related aspect, are used for immunizing animals for the generation of antibodies and for providing the starter cells and cell lines, respectively, for the generation of hybridoma cell lines as is known to the person skilled in the art. It will be acknowledged by the person skilled in the art that such hybridomas can be further cultivated and further selected. It is accordingly, also within the present invention that the polypeptides according to the present invention and the active and inactive HPGGT according to the present invention are used in a screening assay so as to identify those hybridoma cell lines which produce the antibodies directed to and/or specifically binding with the polypeptides according to the present invention and the inactive HPGGT according to the present invention. Specifically, hybridomas can be selected by applying the HPGGT activity assay for screening in order to identify hybridomas producing antibodies which will abrogate catalytic and inhibitory function of HPGGT.

In a further aspect the present invention is related to a nucleic acid coding for the polypeptides according to the present invention and the inactive HPGGT according to the present invention. It will be acknowledged by the person skilled in the art that knowing the genetic code and, optionally the codon usage in a host organism to express such nucleic acid, such person skilled in the art may prepare such nucleic acid. In a further aspect, the nucleic acid is contained in a vector, preferably an expression vector. In an embodiment, the term vector comprises plasmids, cosmids, viruses, bacteriophages and other vectors usually used in the field of genetic engineering. In a still further aspect, the present invention is related to a host organism containing such vector. In an embodiment, the host organism and in particular the host cell is a recombinant host cell transiently or stably containing the nucleic acid molecules or vectors of the invention. A host cell or host organism is understood to be an organism that is capable to take up in vitro recombinant DNA and, if the case may be, to synthesize the proteins encoded by the nucleic acid molecules of the invention. Preferably, these cells are prokaryotic or eukaryotic cells, for example mammalian cells, bacterial cells, insect cells or yeast cells. The host cells of the invention are preferably characterized by the fact that the introduced nucleic acid molecule of the invention either is heterologous with regard to the transformed cell, i.e. that it does not naturally occur in these cells, or is localized at a place in the genome different from that of the corresponding naturally occurring sequence.

A further embodiment of the invention relates to isolated proteins exhibiting biological properties of HPgGT, preferably HPgGT wherein the normally occurring secretion sequence has been removed or is non-functional, and being encoded by the nucleic acid molecules of the invention, as well as to methods for their production, whereby, e.g. a host cell of the invention is cultivated under conditions allowing the synthesis of the protein and the protein is subsequently isolated from the cultivated cells and/or the culture medium. Isolation and purification of the recombinantly produced proteins may be carried out by conventional means including preparative chromatography and affinity and immunological separations involving affinity chromatography with monoclonal or polyclonal antibodies. As used herein, the term "isolated protein" includes proteins substantially free of other proteins, nucleic acids, lipids, carbohydrates or other materials with which it is naturally associated. Such proteins however not only comprise recombinantly produced proteins but include isolated naturally occurring proteins, synthetically produced proteins, or proteins produced by a combination of these methods. Means for preparing such proteins are well understood in the art. The proteins of the invention are preferably in a substantially purified form.

Thus, the present invention also relates to a general method of making a protein in prokaryotic or eukaryotic host cells, which is harmful for said cells when externally applied, comprising: (a) culturing a host cell transfected with a nucleic acid sequence encoding said protein with a deleted or non-functional secretory signal sequence under conditions such that said protein is expressed; and (b) recovering said protein from the cells. The same applies also to a host cell transfected with a nucleic acid encoding the polypeptides according to the present invention which can be recovered from said cells.

It will be understood that the antibodies, anticalines, peptide aptamers, apatmers and spiegelmers according to the present invention may preferably be regarded as ligands to the gamma glutamyl transpeptidase of *Helicobacter pylori* (HPGGT).

Within the present invention the term wild type HPGGT or similar expressions preferably refer to HPGGT of the wild type which is lacking the secretion sequence, but is catalytically active, more specifically catalyses the enzymatic reaction described herein for HPGGT.

The present invention will now be further illustrated by the figures and examples from which further features, embodiments and advantages may be taken.

FIG. 1A is a table indicating secreted proteins from *H. pylori* with a molecular weight between 30 and 66 kDa according to Kim et al. and Bumann et al.[9,10]

FIG. 1B is an SDS-PAGE after silver staining indicating proteins in eluted fractions from size-exclusion chromatography, whereby only fractions b-f inhibited proliferation of human T cells, whereas all other fractions did not; protein bands corresponding to the inhibitory profile of the fractions are marked by arrows.

FIG. 1C is a bar diagram representing enzymatic GGT activity of gelfiltration fractions which was determined by a spectrophotometric assay as described in example 1. (HP=*H. pylori*)

FIGS. 2A to C are bar diagrams showing cell proliferation of stimulated PBMC (A) and isolated primary human T lymphocytes (C) in the presence or absence of indicated HPSN which was determined by $^3$H-Thymidine incorporation assay; GGT phenotype of constructed knock-out strains was confirmed by enzyme activity assay and immunoblotting using a polyclonal antibody raised against the large GGT-subunit (B). For immunoblotting 30 μg protein of HPSN were used. Immunoblotting with anti-VacA antibody served as a loading control (see insert). Data represent mean±SD of 3 independent experiments. *P values<0.001 as determined by Student t-test were considered significant. (HP=*H. pylori*, SN=supernatant, WT=wild-type).

FIGS. 3A and B depict a gel after silver staining (A) and immuno blotting (B) of purified recombinant HPGGT fractions with anti-GGT antibody directed against its large subunit show processing of GGT. Asterisks indicate: * pro-form,  large and * small subunit.

FIGS. 3C to 3E are bar diagrams showing the enzymatic activity (C) and proliferation inhibition of human PBMC (D) by recombinant HPGGT (rHPGGT) expressed in *E. coli*. LPS from *E. coli* used as a control did not inhibit PBMC proliferation. Recombinant HPGGT showed catalytic activity at pH 2-10 (E). Data represent mean±SD of 3 independent experiments. *P value<0.001 as determined by Student t-test was considered significant. (FT=Flow-through, HP=*H. pylori*).

FIGS. 4A to D are bar diagrams indicating that purified GGT from equine kidney displayed catalytic GGT activity (A) but lacked proliferation-inhibiting effect towards lymphocytes (B). Site-directed mutagenesis of recombinant HPGGT at Ser 451/452 (S451/452A) abolished GGT enzyme activity (A) and the inhibitory effect (B). Preincubation of HPWTSN with acivicin (50 μM) for 2 h at 37° C. abrogated GGT activity (C) and inhibition of PBMC proliferation (D). Data represent mean±SD of 3 independent experiments. *P values<0.05 as determined by Student t-test were considered significant. (HP=*H. pylori*, SN=supernatant, WT=wild-type).

Figure 5:
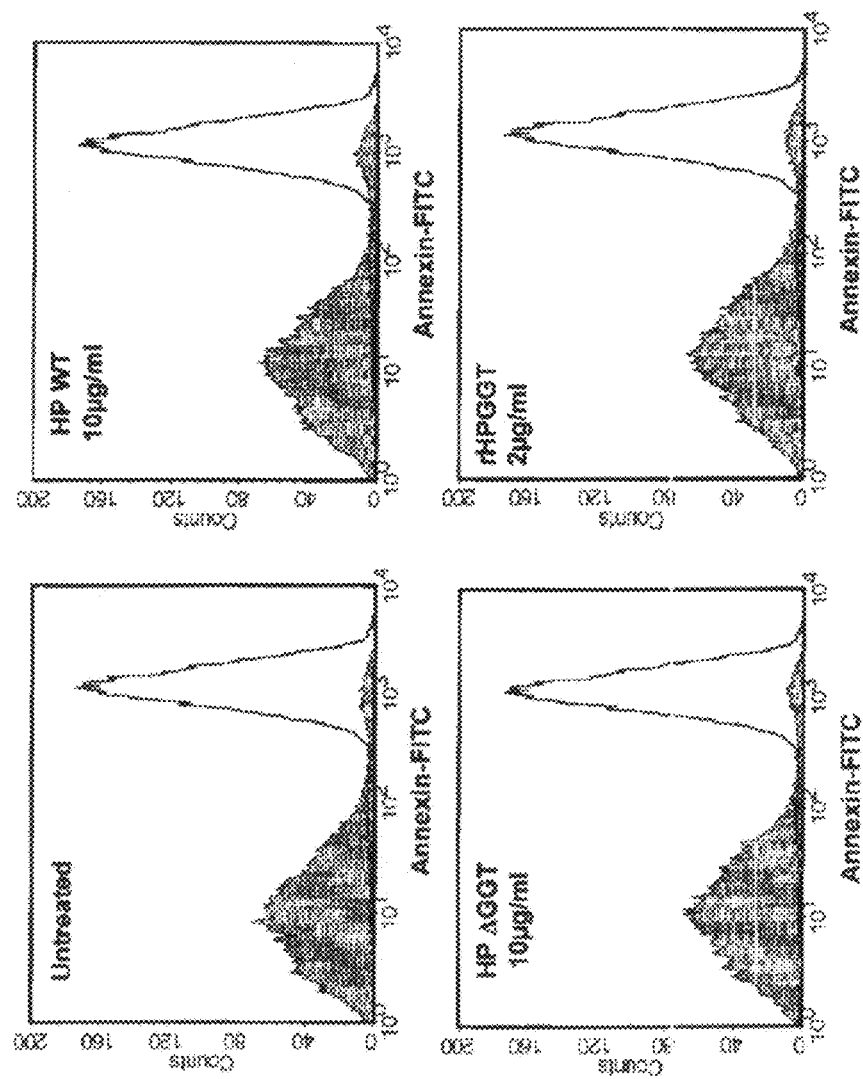

FIGS. 5A and B are diagrams indicating the production of cytokines IL-2 (A) and IFN-γ (B) by PBMC which was measured after 24 h by ELISA as described in example. Data represent mean±SD of 3 independent experiments. P values as determined by Student t-test are indicated.

FIG. 5C depicts the result of a FACS-analysis of Jurkat T cells which were treated for 24 h as indicated (grey curves) and stained with Annexin V-FITC and propidium iodide. The rate of apoptotic Jurkat T cells was determined by FACS-analysis acquiring 10000 events. The anti-cancer drug staurosporin (blank curve), used as a positive control, strongly induced apoptosis at a concentration of 1 μM. (HP=*H. pylori*, WT=wild-type).

Figure 6:
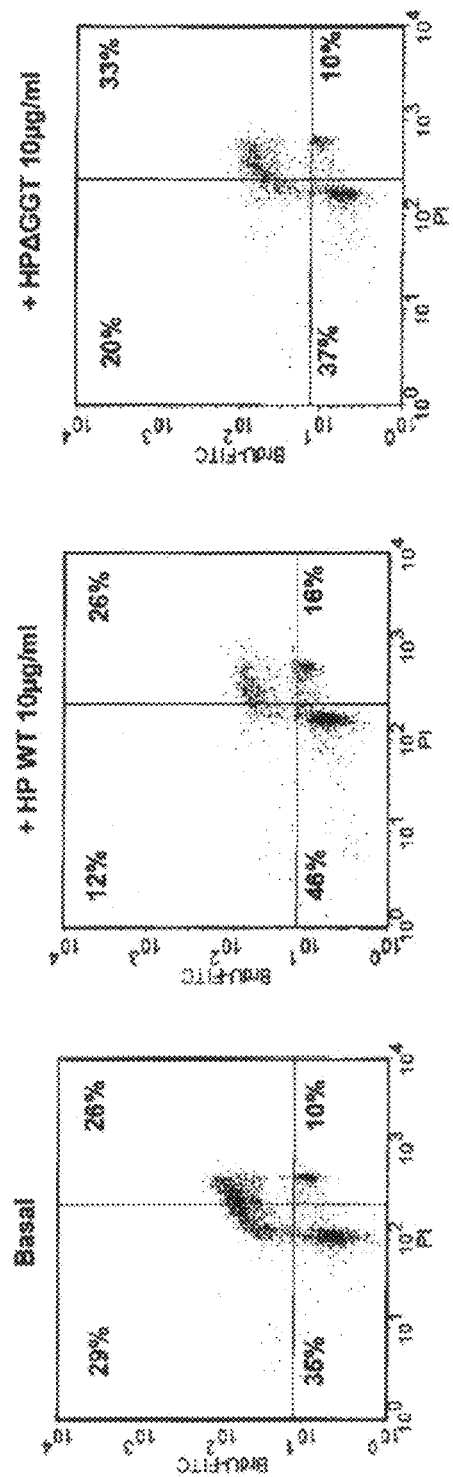

FIG. 6A shows the result of a cell cycle analysis of Jurkat T cells treated with or without indicated HPSN for 24 h. Percentage of cells in G1- (lower left), early and late S- (upper left and right) and G2-phase (lower right) is depicted (y-axis: BrdU-FITC; x-axis: PI). Cellular levels of cell cycle regulatory proteins were determined in the same cells by immunoblotting.

FIG. 6B an SDS PAGE of the proteins obtained from $10^7$ PBMC which were incubated with different concentrations of HPWT and HPΔGGTSN or rHPGGT for 24 h and 48 h and subsequently lysed. 35 μg of total protein were separated by SDS-PAGE and analyzed by immunoblotting. Levels of indicated proteins were determined using the corresponding antibodies. Data were reproduced 2 times with similar results. (HP=*H. pylori*, SN=supernatant, WT=wild-type).

Figure 7:
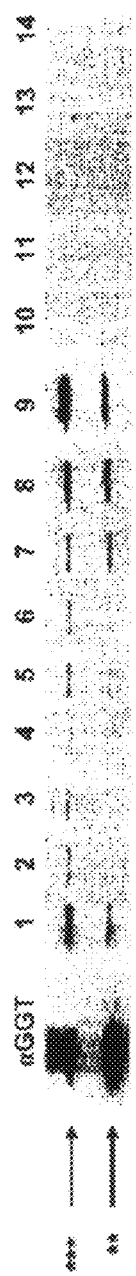

FIG. 7 is an immuno blot of Sera from *H. pylori* positive (lanes 1-9) and negative (lanes 10-14), whereby patients were tested for the presence of antibodies directed against HPGGT by immunoblotting as described in Example 1. Rabbit anti-GGT antibody (αGGT) was used as a positive control. Asterisks indicate: * pro-form and  large subunit of HPGGT protein.

Figure 8:
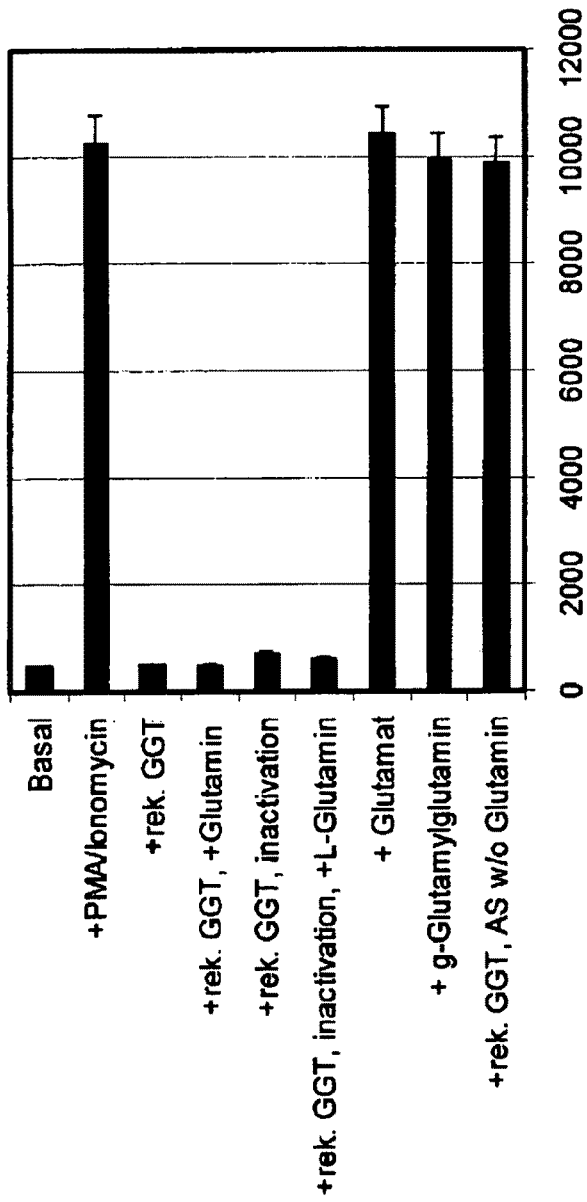

FIG. 8 is a bar diagram indication the inhibition of lymphocyte proliferation by HPGGT depends on Glutamin, but is not mediated by Glutamat or g-Glutamylglutamin, nor by Glutamin depletion. PBMC were stimulated with PMA/Ionomycin (all except basal) and treated as indicated. Rek. HPGGT as used at 2 μg/ml was inactivated after 24 hours. Then, medium was changed and the HPGGT-treated medium was added to the PBMCs after stimulation. Glutamin was added at 2 mM at the same time (not shown) or also after 24 hours to investigate possible glutamine depletion. Glutamat or g-glutamylglutamin were added after BPMC stimulation to investigate possible inhibitory effects. Aminoacids without (w/o) Glutamin were used to show the dependency of the inhibitory effect on glutamin.

Figure 9:
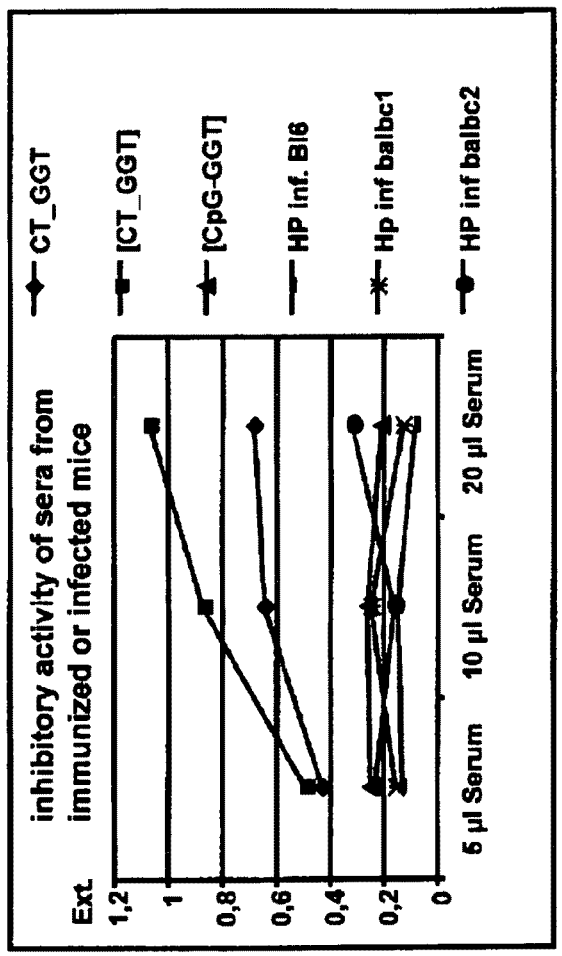

FIG. 9 is a diagram indicating the inhibitory effect of sera from immunized or infected mice on enzymatic activity of HPGGT. Mice were immunized with the indicated formulations or received PBS as control or were infected with live *H. pylori*. Sera were taken from tail veins 6 weeks after immunization or infection and assayed for inhibitory activity towards GGT catalytic activity. CT_GGT, soluble CT and inactive GGT Protein, [CT_GGT]enc, CT and inactive GGT protein encapsulated in microspheres.

EXAMPLE 1

Materials and Methods

Bacteria Culture.
The *H. pylori* wild-type strain G27 WT (vacA$^+$ cagA$^+$) used in this study was obtained from A. Covacci (IRIS, Siena, Italy). The bacteria were cultured on Wilkins-Chalgren or Brain-Heart-Infusion (BHI) plates supplemented with Dent supplement antibiotic mix (Oxoid, Wesel, Germany) as previously described.[29] Liquid culture of HP was performed in BHI broth supplemented with 10% FCS (Sigma, Munich, Germany) and 1% Dent supplement. For production of HP supernatants the bacteria were grown on plates for 48 h, washed 3 times in phosphate buffered saline (PBS) and adjusted to $OD_{600\ nm}$ of 1 (corresponding to approx. $2\times10^8$ bacteria/ml). The bacteria were incubated in PBS for 2 h under microaerophilic conditions with vigorous shaking and pelleted by subsequent centrifugation steps at 3000×g and 10000×g to remove bacteria and membranes. Subsequently, supernatants were concentrated using ultrafiltration (Amicon Ultra MWCO 10 kDa, Millipore, Schwalbach, Germany). The total protein content of the supernatants was measured by Bradford assay (Bio-Rad Laboratories, Richmond, Va.) with bovine serum albumin as standard and stored at −80° C. *E. coli* were cultured on Luria broth (LB) agar plates (USB, Cleveland, Ohio) and for liquid culture in LB broth (USB) with relevant antibiotics.

Gelfiltration Chromatography of *H. pylori* Supernatants.

Supernatants from *H. pylori* wild-type strain G27 were prepared as described above. Size exclusion chromatography was performed as described before[3]. Briefly, 500 µg of protein were loaded on a Superdex 200 10/300 column (GE Healthcare, Munich, Germany) and eluted with degassed PBS at 4° C. Standard proteins α-amylase (200 kDa), alcohol dehydrogenase (150 kDa), bovine serum albumin (66 kDa), and carbonic anhydrase (29 kDa) were used for molecular weight estimation of eluted proteins. Each fraction was tested for proliferation inhibition and GGT activity as described below.

Generation of GGT Mutant Strains.

The GGT k.o. plasmid was transformed to *H. pylori* strain G27 by natural transformation. Transformants were incubated on agar plates containing 25 µg/ml kanamycin (Sigma). After 3 days clones were picked and spread on fresh agar plates with kanamycin. Insertion of the plasmid was verified by PCR (Primer: sense 5'-AAACGATTGGCTTGGGTGT-GATAG-3' (SEQ. ID. No. 6); antisense 5'-GACCGGCTTAG-TAACGATTTGATAG-3' (SEQ. ID. No. 7)) of bacterial DNA and Western Blotting of proteins from *H. pylori* ΔGGT supernatants.

Cell Culture:

Isolation of peripheral blood lymphocytes (PBMC) was performed as described previously[3]. All cells were incubated at 37° C. with 5% $CO_2$. Jurkat T cells and PBMC were cultured in RPMI 1640 (Invitrogen, Karlsruhe, Germany) with 10% FCS. EL-4 T cells were cultured in DMEM (Invitrogen) supplemented with 10% horse serum (Cambrex, Verviers, Belgium).

Isolation of Primary Human T Lymphocytes.

Primary human T cells were isolated from buffy coats or heparinized peripheral venous blood from *H. pylori*-uninfected healthy volunteers by negative selection using the Pan T cell Isolation Kit II (Miltenyi Biotech, Bergisch Gladbach, Germany) according to the manufacturer's instructions.

Cell Proliferation Assays:

Cells ($10^5$ PBMC, purified primary T cells or $10^4$ Jurkat/EL-4 cells/well) were cultured in 96-well flat-bottom plates in complete medium. PBMC were stimulated in triplicate with PMA (20 ng/ml; Sigma) and Ionomycin (100 ng/ml; Sigma) and all cells were grown with or without indicated total protein concentrations of *H. pylori* supernatants or recombinant proteins. Primary human T cells were stimulated with either PMA/Ionomycin as described above or with anti-CD3/CD28 beads (Invitrogen) at 1 bead per T cell. Cellular proliferation was determined after 48 h by methyl-[$^3$H]-thymidine (GE Healthcare) incorporation using a Packard Direct Beta Counter Matrix 9600 (Packard Instruments Co, Downer's Grove, Ill.).

Preparation of Recombinant Proteins.

The GGT protein of *H. pylori* was expressed as 6× His-tagged protein according to the manufacturer's instructions (Qiagen, Hilden, Germany). The coding region of the GGT protein from *H. pylori* was amplified by PCR (primer sense: 5'-TGAAAGGAAAACCCATGGGACGGAG-3' (SEQ: ID. No. 8); antisense: 5'-CAAAGGTACCAAATTCTTTCCT-TGG-3' (SEQ. ID. No. 9)). The PCR product was separated by agarose gel electrophoresis and purified by gel extraction (Qiagen). It was then restricted with NcoI and KpnI (New England Biolabs, Ipswich, Mass.) followed by ligation into the pQE-Tri System vector (Qiagen) after re-purification. The resulting vector was transformed into *E. coli* strain M15. LB broth supplemented with 100 µg/ml ampicillin (Sigma) and 25 µg/ml kanamycin was inoculated with an overnight culture of transformed bacteria and grown at 37° C. with vigorous shaking until $OD_{600}$ reached 0.6. Expression of recombinant HPGGT was induced by adding Isopropyl β-D-1-thiogalactopyranoside (IPTG; Applichem, Darmstadt, Germany) at a final concentration of 1 mM and was performed for 4 h at 25° C. to minimize the amount of inclusion bodies. Afterwards the whole culture was centrifuged (5000×g) for 10 min at 4° C. For lysis under native conditions pellets were solubilised in ice-cold binding buffer (20 mM Tris/HCl, 500 mM NaCl, 20 mM imidazole (Sigma), pH 7.4) containing protease inhibitors (Protease inhibitor cocktail for His-tagged proteins, Sigma). Cells were then lysed by two freeze & thaw cycles in liquid $N_2$ and subsequent sonication (2×1 min sonication with 5 min break on ice between) on ice. After centrifugation (17500×g at 4° C.) for 10 min the supernatant was submitted to DNA and RNA digestion. After a further centrifugation step (22000×g for 10 min at 4° C.) supernatants were prepared for purification. In the first purification step 5 ml His-TrapHP columns (GE Healthcare) were used. Purification was carried out at RT and samples were kept on ice throughout. Lysate of *E. coli* was loaded on Ni-sepharose column at 1 ml/min and flowthrough was collected. After sample loading the column was washed with ten column volumes (cv) binding buffer, ten cv wash buffer (20 mM Tris/HCl, 900 mM NaCl, 20 mM imidazole, pH 7.4) and another ten cv binding buffer. Bound protein was eluted with elution buffer (20 mM Tris/HCl, 500 mM NaCl, 100-1000 mM imidazole, pH 7.4) using a stepwise imidazole gradient (100 mM steps). Eluates were collected in one fraction per step of gradient. Each fraction was then tested for GGT enzyme activity and processed to SDS-PAGE and immunoblot analysis. For further purification of recombinant HPGGT, enzymatically active fractions from Ni-sepharose affinity chromatography were pooled, dialyzed for 1 h against 20 mM Tris/HCl pH 7.5 at 4° C. and processed to the second purification step. The dialyzed sample was loaded on an Affi-Gel® Blue (BioRad) column (cv: 12.3 ml). The column was washed with two cv of binding buffer and bound protein was eluted with elution buffer (20 mM Tris/HCl, 50-1000 mM NaCl, pH 7.5) using a stepwise NaCl gradient (50 mM steps). All collected fractions were analyzed by immunoblotting using anti-GGT antibody (see below) and by GGT enzyme activity assay (see below) for presence of recombinant HPGGT. Active fractions were pooled, dialyzed against 20 mM Tris/HCl pH 7.5 for 90 min at 4° C., aliquoted and stored at −80° C. until further use.

Site Directed Mutagenesis.

Site-directed mutagenesis of HPGGT was performed with a QuikChange site-directed mutagenesis kit (Stratagene, Amsterdam, The Netherlands) according to the manufacturer's protocol. Primer sequences were as follows: S451/452A sense: 5'-CCAATAAGCGCCCTTTAGCCGCCAT-GTCGCCTACGATTGTG-3' (SEQ. ID:No. 10); S451/452A antisense: 5'-CACAATCGTAGGCGACATGGCG-GCTAAAGGGCGCTTATTGG-3' (SEQ:ID:No. 11). Successful mutagenesis was confirmed by sequencing.

Immunoblotting.

For immunoblot analysis $10^7$ Jurkat T cells or PBMC were used. Prior to the experiment, Jurkat cells were serum starved for 18 h in medium containing 0.2% FCS. Afterwards, cells were released with 10% FCS and treated as depicted. At the indicated time points, the cells were harvested, washed once with ice-cold PBS, resuspended in 1× lysis buffer (Cell Signaling Technology, Danvers, Mass.) containing protease inhibitors (2.5 mM sodium pyrophosphate, 1 mM β-glycerophosphate, 1 mM $Na_3VO_4$, 1 µg/ml leupeptin, 1 mM PMSF; Sigma) and sonicated with a micro tip sonifier on ice for 30 sec. Lysates were centrifuged at 10000×g for 10 min at 4° C. and supernatants were used for immunoblotting. Equal amounts of protein (determined by Bradford assay, BioRad) were separated by Tricine-SDS-PAGE and electrotransferred onto nitrocellulose membranes (BioRad). For detection, membranes were probed with primary antibodies anti-p27, anti-Cyclin D3, anti-Cyclin E, anti-c-Myc (Dianova, Hamburg, Germany), anti-Cdk2 (Santa-Cruz Biotechnology, Heidelberg, Germany), anti-phospho-AKT (Ser 473), anti-phospho-c-Raf (Ser 338), anti-phospho-p70S6K (Thr 389; Cell Signaling), anti-phospho-FKHRL1/Foxo3 (Thr 32; Upstate, Lake Placid, N.Y.), anti-Actin (Sigma) and anti-VacA (Austral Biologicals, San Ramon, Calif.). Binding of primary antibodies was revealed using appropriate peroxidase conjugated secondary antibodies (Dianova) and chemiluminescent reagents (Perbio Science, Bonn, Germany). For detection of the large subunit of the HPGGT protein a polyclonal rabbit anti-GGT antibody raised against a synthesized peptide IQPDTVTPSSQIKPGM including amino acid residues 356 to 371 of the HP 1118 gene product (Charles River, Kisslegg, Germany) was used.

Serum Blotting.

For detection of HPGGT specific antibodies in human sera, 0.1 µg of purified recombinant HPGGT protein was separated by SDS-PAGE and transferred onto nitrocellulose membranes as described above. The membrane was stained with Ponceau S solution (0.2% Ponceaus S, 3% trichloroacetic acid in $H_2O$) and cut into stripes. After blocking (1×TBS+5% low fat dry milk) each stripe was incubated with serum (diluted 1:20000 in blocking buffer) of *H. pylori*-infected and uninfected patients, respectively, at 4° C. with agitation over night. After washing, membrane stripes were incubated with HRP-conjugated anti-rabbit secondary antibody (Dianova; dilution 1:10000) and finally, after another washing step, binding of serum antibodies to HPGGT protein was revealed by chemiluminescence reaction as described above. Patients' status of *H. pylori* infection was assessed using conventional *H. pylori* IgG ELISA.

Cell Cycle Analysis.

Prior to analysis, Jurkat T cells (5×10⁶ cells/analysis) were serum starved for 18 h in medium containing 0.2% FCS. After release with 10% FCS and treatment of cells with indicated supernatants of *H. pylori* strains for 24 h, cell-cycle analysis was performed by BrdU-FITC/PI (Sigma) staining according to the manufacturer's protocol using a FITC-conjugated anti-BrdU antibody (BD Bioscience, Heidelberg, Germany). During subsequent fluorescence-activated cell sorter (FACS) analysis, using a Becton-Dickinson FACScan flow cytometer, 10000 events were acquired. Data were analyzed using the Cell Quest software package (BD Biosciences).

γ-Glutamyl Transpeptidase (GGT) Activity Assay.

The assay for GGT activity was adapted from the method of Meister et al.[27] Briefly, reaction buffer consisting of 20 mM glycyl-glycine (Sigma) as acceptor, 2.5 mM L-γ-glutamyl-p-nitroanilide (Calbiochem, Schwalbach, Germany) as donor substrate and 100 mM Tris-HCl (pH 8.0) was prepared. In some experiments pH of assay buffer was varied between 2 and 10. Supernatants of different *H. pylori* strains, purified recombinant HPGGT or equine kidney GGT (Sigma) were added and the reaction proceeded at 37° C. for 30 min. The release of p-nitroanilide was monitored by spectrophotometry at 405 nm. One unit of activity was defined as the quantity of enzyme that released 1 µmol of p-nitroanilide per min and per mg of protein at 37° C.

ELISA.

PBMC (5×10⁵ each) were treated for 24 h as depicted. At indicated time points cells were removed by centrifugation and supernatants were analyzed for amounts of IL-2 (eBioscience, San Diego, Calif.) and IFN-γ (Biosource, Solingen, Germany) by ELISA according to the manufacturer's instructions. The lower limits of detection were 4 pg/ml.

Analysis of Apoptosis.

5×10⁵ Jurkat T cells were treated as indicated. After 24 h cells were harvested by centrifugation, washed, resuspended in 500 µl AnnexinV-binding buffer (10 mM HEPES/NaOH, pH7.4, 140 mM NaCl, 2.5 mM $CaCl_2$) and stained for 10 min each with 5 µl recombinant Annexin V-FITC (Caltag, Burlingame, Calif.) and 0.5 µg/ml PI at room temperature in the dark. Apoptotic cells were measured by FACS analysis (see above). Data were analyzed using Cell Quest software.

Statistics.

Data are presented as mean±standard deviation (SD). For statistical analysis the Student t-test was used. P-values<0.05 were considered significant.

EXAMPLE 2

Identification of GGT as a Putative T Cell Proliferation Inhibiting Protein of *H. pylori*

It was previously shown that a secreted low-molecular weight protein from *H. pylori* inhibits proliferation of T lymphocytes.[3] To identify the immunosuppressive factor, size-exclusion chromatography with supernatants from *H. pylori* strain G27 was performed. In line with the previous work only fractions eluting with a molecular weight between 30-66 kDa inhibited proliferation of lymphocytes, whereas all the other fractions did not (data not shown).

Two independent groups previously performed a systematic analysis of secreted *H. pylori* proteins by different proteomics techniques.[9,10] Using these data all secreted *H. pylori* proteins with a molecular weight between 30 and 66 kDa were listed (FIG. 1A). Proteins of obtained chromatographic fractions were further analysed by SDS-PAGE and silver staining (FIG. 1A). Four potential candidates with a size between 30 and 66 kDa were found, which displayed an elution profile matching inhibitory activity profile of the fractions (FIG. 1B; indicated by arrows). All other protein bands in the inhibiting fractions were also present in the non-inhibiting fractions and could therefore not be responsible for inhibition of T cell proliferation. The molecular weights of two of the four candidate proteins (FIG. 1B) corresponded to fragments of the secreted *H. pylori* protein γ-glutamyl transpeptidase (GGT, HP1118). The first band at 60 kDa might represent the GGT pro-form (MW 61 kDa) and the other one at 38 kDa the large subunit of the GGT.[11] To investigate the presence of catalytically active HPGGT in these supernatant fractions, a photometric GGT activity assay was performed. FIG. 1C shows that only fractions inhibiting lymphocyte proliferation (b-f) also display GGT activity.

EXAMPLE 3

GGT-Deficient *H. pylori* Mutants Lack Ability to Suppress T Cell Proliferation

To determine whether GGT was responsible for the observed inhibition of lymphocyte proliferation, isogenic GGT knock-out mutants of *H. pylori* were generated. The mutants grew normally in vitro as described by other groups, indicating that GGT is not essential for survival of *H. pylori*.[11,12,13] Supernatants of these mutants were tested for their proliferation inhibiting activity towards isolated human T cells and PBMC, stimulated with anti-CD3/CD28 or PMA/Ionomycin, in comparison to the corresponding wild-type strain (FIG. 2A, C). In contrast to the wild-type strain the inhibitory potential of ΔGGT bacteria towards primary human T cells and PBMC was completely abrogated. To exclude spontaneous recombination and reactivation of the GGT, supernatants from GGT-deficient bacteria were verified by measuring enzyme activity and by immunoblotting using a polyclonal antibody that we raised against the large subunit of HPGGT. The loading control shows the presence of secreted VacA protein in supernatants from wild-type and GGT-deficient bacteria (FIG. 2B). Thus, GGT is responsible for inhibition of T cell proliferation by *Helicobacter pylori*.

EXAMPLE 4

Recombinant HPGGT Inhibits Proliferation of Lymphocytes

To further show that the observed inhibition was mediated solely by the HPGGT, a recombinant His-tagged HPGGT protein in *E. coli* was expressed. The protein was purified to homogeneity by chromatography as described in the "Materials and Methods" section. SDS-PAGE and silver staining as well as immunoblotting indicated that the recombinant HPGGT was synthesized as a pro-form and subsequently processed into a large and small subunit with molecular weights of ~38 and ~20 kDa, respectively (FIG. 3A, B). The recombinant protein showed strong GGT activity (FIG. 3C) and efficiently inhibited PBMC proliferation (FIG. 3D). In addition, further experiments showed catalytic activity of the HPGGT at a pH range of 2-10 (FIG. 3E) supporting the presence of the functional enzyme at the site of infection.

EXAMPLE 5

The Inhibitory effect of HPGGT Depends on Catalytic GGT Activity

As the GGT is also expressed by mammalian cells including human T cells we tended to determine whether a mammalian GGT also inhibited lymphocyte proliferation. Purified GGT from equine kidney displayed catalytic activity (FIG. 4A). However, even a fourfold higher amount of equine GGT in comparison to HPGGT failed to inhibit PBMC proliferation (FIG. 4B). To explore whether the catalytic transpeptidase activity of GGT was required for inhibition of T cell proliferation, we generated a mutant of the recombinant protein. We found that mutagenesis of serine residues 451 and 452 to alanine (S451/452A) completely abolished the enzymatic activity of recombinant HPGGT (FIG. 4A) and also abrogated inhibition of lymphocyte proliferation (FIG. 4B).

To confirm these results, recombinant HPGGT and supernatants from *H. pylori* wild-type strain G27 were preincubated with the GGT inhibitor acivicin. This compound acts as an irreversible and competitive inhibitor of GGT. Inhibition of GGT by acivicin was shown to involve its transformation after binding to the enzyme in an inhibitory species attached to a specific hydroxyl group of GGT.[14,15] Measurement of enzymatic GGT activity and determination of lymphocyte proliferation showed that pretreatment with acivicin completely repressed GGT activity (FIG. 4C) and the inhibition of PBMC proliferation (FIG. 4D) by *H. pylori* wild-type supernatants. Similar results were obtained for recombinant HPGGT (data not shown).

EXAMPLE 6

HPGGT Inhibits Lymphocyte Proliferation Without Reducing IL-2- and IFNγ-Secretion and Without Inducing Apoptosis To date so far nothing was known about a role of HPGGT during suppression of the host's immune response. The inhibition of lymphocyte proliferation by HPGGT reported here might result from interference with cytokine secretion of human PBMCs. To test this hypothesis, cells were stimulated with PMA and Ionomycin and incubated with or without *H. pylori* wild-type and ΔGGT supernatants or recombinant HPGGT at different concentrations for 24 h. In comparison to the stimulated control, none of these treatments led to reduction of IL-2 secretion (FIG. 5A), which is known to be essential for proliferation of lymphocytes. In addition secretion of IFN-γ was not reduced (FIG. 5B). Thus, we show that inhibition of T cell proliferation by HPGGT is not caused by diminished activation of these cells. Previous reports suggested induction of oxidative stress and apoptosis by HPGGT in gastric epithelial cells.[12,16] However, nothing is known about the effect of GGT from *H. pylori* towards lymphocytes.

Additional reports suggested the induction of apoptosis in T cells by *H. pylori* as a mechanism for inhibition of T cell proliferation by the bacteria (Wang et al J Immunol 2001). To examine the possibility that apoptosis is responsible for reduction of lymphocyte proliferation by HPGGT described here, Annexin V-FITC/PI staining and subsequent FACS analysis using Jurkat T cells was performed (FIG. 5C). Neither supernatants from *H. pylori* wild-type and ΔGGT strain nor recombinant HPGGT used in concentrations, which caused a strong inhibition of lymphocyte proliferation, induced an increase in apoptosis. Hence, abrogation of T cell proliferation by the HPGGT is mediated by an apoptosis-independent mechanism.

EXAMPLE 7

Effect of HPGGT on Cell Cycle Progression in T Cells

Next we sought to further characterize the effect of HPGGT on cellular processes involved in proliferation of T cells. Analysis using BrdU/PI-staining showed a G1 cell cycle arrest in Jurkat T cells induced by wild type but not by GGT-deficient supernatants from *H. pylori* (FIG. 6A). This arrest was characterized by an increase of cells in G1 phase (FIG. 6A; lower left quadrant) in the presence of *H. pylori* GGT from 35 to 46%. Accordingly the amount of cells in S-phase (upper left and right quadrants) was reduced to 38% in comparison to the control (Basal, 55%) during treatment with wild-type but not GGT-deficient supernatants of *H. pylori*. In line with this, immunoblot analysis of the same samples revealed a pronounced reduction of cellular Cyclin D3 as well as E1 protein levels. In addition, the amount of the Cdk-inhibitor p27Kip1 was elevated in a GGT-dependent manner (FIG. 6A). The difference in Cyclin protein levels between cells treated with 10 and 5 μg/ml of HP WT supernatant indicates that a threshold of GGT activity has to be exceeded to antagonize lymphocyte proliferation. This is obviously the case at a concentration of 10 μg/ml of total protein in the supernatant. At lower concentrations of 5 μg/ml it takes longer for the GGT to inhibit cell-cycle progression in lymphocytes. Using the recombinant HPGGT protein, we observed complete reduction of Cyclin levels at a concentration as low as 2 μg/ml These results were confirmed on human PBMCs, which exhibited an even stronger reduction of the same cell cycle regulating proteins (FIG. 6B) when treated with recombinant HPGGT or different concentrations of supernatants from *H. pylori* wild type but not ΔGGT strains. Our results clearly point to GGT as being the factor responsible for induction of a G1 cell cycle arrest in T lymphocytes by *H. pylori*.

EXAMPLE 8

Interference of HPGGT with Ras-Dependent Signaling in T Cells

The Ras- and PI3K-dependent pathways are key regulators of cell-cycle progression. As these pathways have been shown to proceed independently of each other in T cells[17], we investigated the influence of *H. pylori* supernatants as well as recombinant HPGGT on the activation status of important members of both pathways. Immunoblot analysis of cell lysates from Jurkat T cells and PBMC showed that cellular levels and phosphorylation of AKT, p70S6k and Foxo 3, important mediators of PI3K-signaling were not reduced in the presence of HPGGT (FIG. 6A). In contrast, cellular levels of c-Myc as well as phosphorylation of c-Raf protein, central mediators of the Ras-dependent pathway, were reduced in the presence of HPGGT in the same cells (FIG. 6A, B).

EXAMPLE 9

Antibody Response Towards HPGGT in Sera of HP-Positive Patients

Although GGT from *H. pylori* has been shown to be secreted into the extracellular medium by the bacteria (Bumann et al) it is unclear whether this protein reaches T cells in the lamina propria to exert its immunosuppressive effects. To address this question we tested sera from 14 patients (9 *H. pylori*-infected and 5-uninfected) for the presence of HPGGT specific antibodies. The results showed a strong antibody response towards the pro-form and the large subunit of the HPGGT in *H. pylori*-positive (FIG. 7, 1-9) but not in uninfected patients (FIG. 7, 10-14) suggesting an interaction of HPGGT with the human immune system.

EXAMPLE 10

Inhibitory Immune Response Towards HPGGT after Immunization but not Infection

Animals were vaccinated with eather peptide 356 IQP-DTVTPSSQIKPGM 371 (SEQ. ID. No. 12) positioned at fare distance apart from the catalytic center of the *Helicobacter pylori* gamma-Glutamyl-Transpeptidase (HPGGT) or with inactive recombinant HPGGT protein in combination with CT as adjuvant. Only in the animals vaccinated with the inactive form of HPGGT, inhibitory antibodies in the serum were detectable, using the standard HP gGT activation assay. No inhibitory immune response was detected in control animals which received buffer only, in infected animals or in animals vaccinated with the peptide 356-371. These results prove that an inhibitory immune response against HPGGT can be achieved, and highly depends on the selection of the antigen. Further, infection with *H. pylori* does not elicit such inhibitory response.

The results are shown in FIG. 9.

REFERENCES

The documents of the prior art to which it is referred to herein using numerals are as follows and are incorporated herein by reference in their entirety.

1. Blaser, M. J, Atherton, J. C. *Helicobacter pylori* persistence: biology and disease. J Clin Invest. 2004; 113: 321-333.
2. Ermak T H, Giannasca P J, Nichols R, Myers G A, Nedrud J, Weltzin R, Lee C K, Kleanthous H, Monath T P. Immunization of mice with urease vaccine affords protection against *Helicobacter pylori* infection in the absence of antibodies and is mediated by MHC class II-restricted responses. J Exp Med. 1998; 188: 2277-2288.
3. Gerhard M, Schmees C, Voland P, Endres N, Sander M, Reindl W, Rad R, Oelsner M, Decker T, Mempel M, Hengst L, Prinz C. A secreted low-molecular-weight protein from *Helicobacter pylori* induces cell-cycle arrest of T cells. Gastroenterology. 2005; 128: 1327-1339.
4. Knipp, U., Birkholz, S., Kaup, W., Opferkuch, W. Partial characterization of a cell proliferation-inhibiting protein produced by *Helicobacter pylori*. Infect Immun. 1996; 64: 3491-3496.
5. Gebert, B., Fischer, W., Weiss, E., Hoffmann, R., Haas, R. *Helicobacter pylori* vacuolating cytotoxin inhibits T lymphocyte activation. Science. 2003; 301: 1099-1102.
6. Sundrud, M. S., Torres, V. J., Unutmaz, D., Cover, T. L. Inhibition of primary human T cell proliferation by *Helicobacter pylori* vacuolating toxin (VacA) is independent of VacA effects on IL-2 secretion. Proc Natl Acad Sci USA. 2004; 101: 7727-7732.
7. Atherton, J. C., Peek, R. M. Jr., Tham, K. T., Cover, T. L., Blaser, M. J. Clinical and pathological importance of heterogeneity in vacA, the vacuolating cytotoxin gene of *Helicobacter pylori*. Gastroenterology. 1997; 112: 92-99.
8. Rad R, Gerhard M, Lang R, Schoniger M, Rosch T, Schepp W, Becker I, Wagner H, Prinz C. The *Helicobacter pylori* blood group antigen-binding adhesin facilitates bacterial colonization and augments a nonspecific immune response. J Immunol. 2002; 168: 3033-3041.
9. Kim N, Weeks D L, Shin J M, Scott D R, Young M K, Sachs G. Proteins released by *Helicobacter pylori* in vitro. J Bacteriol. 2002; 184: 6155-6162.
10. Bumann D, Aksu S, Wendland M, Janek K, Zimny-Arndt U, Sabarth N, Meyer T F, Jungblut P R. Proteome analysis of secreted proteins of the gastric pathogen *Helicobacter pylori*. Infect Immun. 2002; 70: 3396-3403.
11. Chevalier, C., Thiberge, J. M., Ferrero, R. L., Labigne, A. Essential role of *Helicobacter pylori* gamma-glutamyl-transpeptidase for the colonization of the gastric mucosa of mice. Mol Microbiol. 1999; 31: 1359-1372.

12. Shibayama K, Kamachi K, Nagata N, Yagi T, Nada T, Doi Y, Shibata N, Yokoyama K, Yamane K, Kato H, Iinuma Y, Arakawa Y. A novel apoptosis-inducing protein from *Helicobacter pylori*. Mol Microbiol. 2003; 47: 443-451.
13. McGovern K J, Blanchard T G, Gutierrez J A, Czinn S J, Krakowka S, Youngman P. Gamma-Glutamyltransferase is a *Helicobacter pylori* virulence factor but is not essential for colonization. Infect Immun. 2001; 69: 4168-4173.
14. Stole, E., Smith, T. K., Manning, J. M., Meister, A. Interaction of gamma-glutamyl transpeptidase with acivicin. J Biol Chem. 1994; 269: 21435-21439.
15. Smith, T. K., Ikeda, Y., Fujii, J., Taniguchi, N., Meister, A. Different sites of acivicin binding and inactivation of gamma-glutamyl transpeptidases. Proc Natl Acad Sci USA. 1995; 92: 2360-2364.
16. Busiello I, Acquaviva R, Di Popolo A, Blanchard T G, Ricci V, Romano M, Zarrilli R. *Helicobacter pylori* gamma-glutamyltranspeptidase upregulates COX-2 and EGF-related peptide expression in human gastric cells. Cell Microbiol. 2004; 6: 255-267.
17. Genot E, Reif K, Beach S, Kramer I, Cantrell D. p21ras initiates Rac-1 but not phosphatidyl inositol 3 kinase/PKB, mediated signaling pathways in T lymphocytes. Oncogene. 1998; 17:1731-1738.
18. Riou, J. Y., Buissiere, J., Richard, C., Guibourdenche, M. gamma-Glutamyl-transferase activity in the family "Neisseriaceae". Ann Microbiol (Paris). 1982; 133: 387-392.
19. Suzuki, H., Kumagai, H., Tochikura, T. Isolation, genetic mapping, and characterization of *Escherichia coli* K-12 mutants lacking gamma-glutamyltranspeptidase. J Bacteriol. 1987; 169: 3926-3931.
20. Xu, K., Strauch, M. A. Identification, sequence, and expression of the gene encoding gamma-glutamyl-transpeptidase in *Bacillus subtilis*. J Bacteriol. 1996; 178: 4319-4322.
21. Ikeda, Y., Fujii, J., Anderson, M. E., Taniguch, i N., Meister, A. Involvement of Ser-451 and Ser-452 in the catalysis of human gamma-glutamyl transpeptidase. J Biol Chem. 1995; 270: 22223-22228.
22. Sherr C J. $G_1$ phase progression: cycling on cue. Cell. 1994; 79: 551-555.
23. Takuwa N, Takuwa Y. Regulation of cell cycle molecules by the Ras effector system. Mol Cell Endocrinol. 2001; 177: 25-33.
24. Sherr C J, Roberts J M. CDK inhibitors: positive and negative regulators of G1-phase progression. Genes Dev. 1999; 13: 1501-1512.
25. Kerkhoff E, Houben R, Loffler S, Troppmair J, Lee J E, Rapp U R. Regulation of c-myc expression by Ras/Raf signaling. Oncogene. 1998; 16: 211-216.
26. Oster S K, Ho C S, Soucie E L, Penn L Z. The myc oncogene: Marvelousl Y Complex. Adv Cancer Res. 2002; 84: 81-154.
27. Meister, A., Tate S. S., Griffith, O. W. Gamma-glutamyl transpeptidase. Methods Enzymol. 1981; 77: 237-253.
28. Glupczynski, Y., Megraud, F., Lopez-Brea, M., Anderson, L. P. European multicenter survey of in vitro antimicrobial resistance in *Helicobacter pylori*. Eur J Clin Microbiol Infect Dis. 2001; 20: 820-823.
29. Gerhard M, Lehn N, Neumayer N, Boren T, Rad R, Schepp W, Miehlke S, Classen M, Prinz C. Clinical relevance of the *Helicobacter pylori* gene for blood-group antigen-binding adhesin. Proc Natl Acad Sci USA. 1999; 96: 12778-12783.
30. Zabaleta J, McGee D J, Zea A H, Hernandez C P, Rodriguez P C, Sierra R A, Correa P, Ochoa A C. *Helicobacter pylori* arginase inhibits T cell proliferation and reduces the expression of the TCR zeta-chain (CD3zeta). J Immunol. 2004 July 1; 173(1):586-93.
31. Boanca G., Sand A., Barycki J. J., Uncoupling the Enzymatic and Autoprocessing Activities of *Helicobacter pylori* gamma-Glutamyltranspeptidas The Journal of Biological Chemistry, Jul. 14, 2006, Vol. 281, No. 28
  Schmees C, Prinz C, Treptau T, Rad R, Hengst L, Voland P, Bauer S, Brenner L, Schmid R M, Gerhard M Inhibition of T cell proliferation by *Helicobacter pylori* γ-glutamyl transpeptidase Gastroenterology 2007 May; 132(5): 1820-33

The features of the present invention disclosed in the specification, the claims and/or the drawings may both separately and in any combination thereof be material for realizing the invention in various forms thereof.

The invention claimed is:

1. An immunogenic composition comprising an inactivated form of gamma glutamyl transpeptidase of *Helicobacter pylori* (HPGGT) having an amino acid sequence according to SEQ ID NO: 1, wherein the serine residues at positions 451 and 452 are replaced by alanine residues.

2. An immunogenic composition comprising a fragment of HPGGT, whereby such fragment consists of a stretch of at least 10 contiguous amino acids comprising amino acids 451 and 452 of gamma glutamyl transpeptidase of *Helicobacter pylori* (HPGGT) according to SEQ ID No: 1, and wherein the serine residues at positions 451 and 452 are replaced by alanine residues.

3. The immunogenic composition according to claim 1, whereby the composition is capable of inducing within an animal or a human being an immune response.

4. The immunogenic composition according to claim 1, whereby the immune response is an antibody response.

5. The immunogenic composition according to claim 1, whereby the immune response comprises antibodies with one or both of (i) an inhibitory effect on gamma glutamyl transpeptidase of *Helicobacter pylori* (HPGGT) and (ii) an abrogating effect on the HPGGT dependent suppression of lymphocyte proliferation.

6. The immunogenic composition according to claim 1, whereby the composition is for promoting activation and proliferation of lymphocytes in a patient suffering from *H. pylori* infection or being at risk of developing an infection with *H. pylori*.

7. The immunogenic composition according to claim 6, whereby the lymphocytes are B or T cells.

8. The immunogenic composition according to claim 1, whereby the composition comprises one or several adjuvants.

9. The immunogenic composition according to claim 1, whereby the composition comprises one or several antigens from *H. pylori*.

10. The immunogenic composition according to claim 9, whereby the antigen is selected from the group comprising outer membrane proteins.

11. The immunogenic composition according to claim 10, whereby the antigen is selected from the group comprising HpaA, Omp18 and combinations thereof.

12. The immunogenic composition according to claim 1, wherein the composition is for the treatment of a disease caused by *H. pylori*.

13. The immunogenic composition according to claim 12, whereby the disease is infection with *H. pylori*.

14. An immunogenic composition as claimed in claim 2, whereby the polypeptide comprises at least 15 contiguous amino acids.

15. The immunogenic composition according to claim 2, whereby the composition is capable of inducing within an animal or a human being an immune response.

16. The immunogenic composition according to claim 2, whereby the immune response is an antibody response.

17. The immunogenic composition according to claim 2, whereby the immune response comprises antibodies with one or both of (i) an inhibitory effect on gamma glutamyl transpeptidase of *Helicobacter pylori* (HPGGT) and (ii) an abrogating effect on the HPGGT dependent suppression of lymphocyte proliferation.

18. The immunogenic composition according to claim 2, whereby the composition is for promoting activation and proliferation of lymphocytes in a patient suffering from *H. pylori* infection or being at risk of developing an infection with *H. pylori*.

19. The immunogenic composition according to claim 18, whereby the lymphocytes are B or T cells.

20. The immunogenic composition according to claim 2, whereby the composition comprises one or several adjuvants.

21. The immunogenic composition according to claim 2, whereby the composition comprises one or several antigens from *H. pylori*.

22. The immunogenic composition according to claim 21, whereby the antigen is selected from the group comprising outer membrane proteins.

23. The immunogenic composition according to claim 22, whereby the antigen is selected from the group comprising HpaA, Omp18 and combinations thereof.

24. The immunogenic composition according to claim 2, wherein the composition is for the treatment of a disease caused by *H. pylori*.

25. The immunogenic composition according to claim 24, whereby the disease is infection with *H. pylori*.

* * * * *

SEQUENCE LISTING

<160> NUMBER OF SEQ ID NOS: 12

<210> SEQ ID NO 1
<211> LENGTH: 567
<212> TYPE: PRT
<213> ORGANISM: Helicobacter pylori

<400> SEQUENCE: 1

Met Arg Arg Ser Phe Leu Lys Thr Ile Gly Leu Gly Val Ile Ala Leu
1               5                   10                  15

Phe Leu Gly Leu Leu Asn Pro Leu Ser Ala Ala Ser Tyr Pro Pro Ile
                20                  25                  30

Lys Asn Thr Lys Val Gly Leu Ala Leu Ser Ser His Pro Leu Ala Ser
            35                  40                  45

Glu Ile Gly Gln Lys Val Leu Glu Glu Gly Gly Asn Ala Ile Asp Ala
        50                  55                  60

Ala Val Ala Ile Gly Phe Ala Leu Ala Val Val His Pro Ala Ala Gly
65                  70                  75                  80

Asn Ile Gly Gly Gly Gly Phe Ala Val Ile His Leu Ala Asn Gly Glu
                85                  90                  95

Asn Val Ala Leu Asp Phe Arg Glu Lys Ala Pro Leu Lys Ala Thr Lys

-continued

Asn Met Phe Leu Asp Lys Gln Gly Asn Val Pro Lys Leu Ser Glu
            115                 120                 125
Asp Gly Tyr Leu Ala Ala Gly Val Pro Gly Thr Val Ala Gly Met Glu
            130                 135                 140
Ala Met Leu Lys Lys Tyr Gly Thr Lys Lys Leu Ser Gln Leu Ile Asp
145                 150                 155                 160
Pro Ala Ile Lys Leu Ala Glu Asn Gly Tyr Ala Ile Ser Gln Arg Gln
                165                 170                 175
Ala Glu Thr Leu Lys Glu Ala Arg Glu Arg Phe Leu Lys Tyr Ser Ser
                180                 185                 190
Ser Lys Lys Tyr Phe Phe Lys Lys Gly His Leu Asp Tyr Gln Glu Gly
                195                 200                 205
Asp Leu Phe Val Gln Lys Asp Leu Ala Lys Thr Leu Asn Gln Ile Lys
                210                 215                 220
Thr Leu Gly Ala Lys Gly Phe Tyr Gln Gly Gln Val Ala Glu Leu Ile
225                 230                 235                 240
Glu Lys Asp Met Lys Lys Asn Gly Gly Ile Ile Thr Lys Glu Asp Leu
                245                 250                 255
Ala Ser Tyr Asn Val Lys Trp Arg Lys Pro Val Val Gly Ser Tyr Arg
                260                 265                 270
Gly Tyr Lys Ile Ile Ser Met Ser Pro Pro Ser Ser Gly Thr His
                275                 280                 285
Leu Ile Gln Ile Leu Asn Val Met Glu Asn Ala Asp Leu Ser Ala Leu
            290                 295                 300
Gly Tyr Gly Ala Ser Lys Asn Ile His Ile Ala Ala Glu Ala Met Arg
305                 310                 315                 320
Gln Ala Tyr Ala Asp Arg Ser Val Tyr Met Gly Asp Ala Asp Phe Val
                325                 330                 335
Ser Val Pro Val Asp Lys Leu Ile Asn Lys Ala Tyr Ala Lys Lys Ile
                340                 345                 350
Phe Asp Thr Ile Gln Pro Asp Thr Val Thr Pro Ser Ser Gln Ile Lys
                355                 360                 365
Pro Gly Met Gly Gln Leu His Glu Gly Ser Asn Thr Thr His Tyr Ser
                370                 375                 380
Val Ala Asp Arg Trp Gly Asn Ala Val Ser Val Thr Tyr Thr Ile Asn
385                 390                 395                 400
Ala Ser Tyr Gly Ser Ala Ala Ser Ile Asp Gly Ala Gly Phe Leu Leu
                405                 410                 415
Asn Asn Glu Met Asp Asp Phe Ser Ile Lys Pro Gly Asn Pro Asn Leu
                420                 425                 430
Tyr Gly Leu Val Gly Gly Asp Ala Asn Ala Ile Glu Ala Asn Lys Arg
                435                 440                 445
Pro Leu Ser Ser Met Ser Pro Thr Ile Val Leu Lys Asn Asn Lys Val
                450                 455                 460
Phe Leu Val Val Gly Ser Pro Gly Gly Ser Arg Ile Ile Thr Thr Val
465                 470                 475                 480
Leu Gln Val Ile Ser Asn Val Ile Asp Tyr Asn Met Asn Ile Ser Glu
                485                 490                 495
Ala Val Ser Ala Pro Arg Phe His Met Gln Trp Leu Pro Asp Glu Leu
                500                 505                 510
Arg Ile Glu Lys Phe Gly Met Pro Ala Asp Val Lys Asp Asn Leu Thr
                515                 520                 525

```
Lys Met Gly Tyr Gln Ile Val Thr Lys Pro Val Met Gly Asp Val Asn
            530                 535                 540

Ala Ile Gln Val Leu Pro Lys Thr Lys Gly Ser Val Phe Tyr Gly Ser
545                 550                 555                 560

Thr Asp Pro Arg Lys Glu Phe
                565

<210> SEQ ID NO 2
<211> LENGTH: 17
<212> TYPE: PRT
<213> ORGANISM: Artificial Sequence
<220> FEATURE:
<223> OTHER INFORMATION: Chemically synthesised

<400> SEQUENCE: 2

Gln Arg Gln Ala Glu Thr Leu Lys Glu Ala Arg Glu Arg Phe Leu Lys
1               5                   10                  15

Tyr

<210> SEQ ID NO 3
<211> LENGTH: 21
<212> TYPE: PRT
<213> ORGANISM: Artificial sequence
<220> FEATURE:
<223> OTHER INFORMATION: Chemically synthesised

<400> SEQUENCE: 3

Phe Asp Ile Lys Pro Gly Asn Pro Asn Leu Tyr Gly Leu Val Gly Gly
1               5                   10                  15

Asp Ala Asn Ala Ile
            20

<210> SEQ ID NO 4
<211> LENGTH: 29
<212> TYPE: PRT
<213> ORGANISM: Artificial Sequence
<220> FEATURE:
<223> OTHER INFORMATION: Chemically synthesised

<400> SEQUENCE: 4

Asp Phe Ser Ile Lys Pro Gly Asn Pro Asn Leu Tyr Gly Leu Val Gly
1               5                   10                  15

Gly Asp Ala Asn Ala Ile Glu Ala Asn Lys Arg Pro Leu
            20                  25

<210> SEQ ID NO 5
<211> LENGTH: 21
<212> TYPE: PRT
<213> ORGANISM: Artificial Sequence
<220> FEATURE:
<223> OTHER INFORMATION: Chemically synthesised

<400> SEQUENCE: 5

Ser Ser Met Ser Pro Thr Ile Val Leu Lys Asn Asn Lys Val Phe Leu
1               5                   10                  15

Val Val Gly Ser Pro
            20

<210> SEQ ID NO 6
<211> LENGTH: 24
<212> TYPE: DNA
<213> ORGANISM: Artificial Sequence
<220> FEATURE:
```

<223> OTHER INFORMATION: Chemically synthesised

<400> SEQUENCE: 6
aaacgattgg cttgggtgtg atag                                           24

<210> SEQ ID NO 7
<211> LENGTH: 25
<212> TYPE: DNA
<213> ORGANISM: Artificial Sequence
<220> FEATURE:
<223> OTHER INFORMATION: Chemically synthesised

<400> SEQUENCE: 7
gaccggctta gtaacgattt gatag                                          25

<210> SEQ ID NO 8
<211> LENGTH: 25
<212> TYPE: DNA
<213> ORGANISM: Artificial Sequence
<220> FEATURE:
<223> OTHER INFORMATION: Chemically synthesised

<400> SEQUENCE: 8
tgaaaggaaa acccatggga cggag                                          25

<210> SEQ ID NO 9
<211> LENGTH: 25
<212> TYPE: DNA
<213> ORGANISM: Artificial Sequence
<220> FEATURE:
<223> OTHER INFORMATION: Chemically synthesised

<400> SEQUENCE: 9
caaaggtacc aaattctttc cttgg                                          25

<210> SEQ ID NO 10
<211> LENGTH: 41
<212> TYPE: DNA
<213> ORGANISM: Artificial Sequence
<220> FEATURE:
<223> OTHER INFORMATION: Chemically synthesised

<400> SEQUENCE: 10
ccaataagcg ccctttagcc gccatgtcgc ctacgattgt g                        41

<210> SEQ ID NO 11
<211> LENGTH: 41
<212> TYPE: DNA
<213> ORGANISM: Artificial Sequence
<220> FEATURE:
<223> OTHER INFORMATION: Chemically synthesised

<400> SEQUENCE: 11
cacaatcgta ggcgacatgg cggctaaagg gcgcttattg g                        41

<210> SEQ ID NO 12
<211> LENGTH: 16
<212> TYPE: PRT
<213> ORGANISM: Artificial Sequence
<220> FEATURE:
<223> OTHER INFORMATION: Chemically synthesised

<400> SEQUENCE: 12

Ile Gln Pro Asp Thr Val Thr Pro Ser Ser Gln Ile Lys Pro Gly Met
1               5                   10                  15